(12) United States Patent
Slawinski et al.

(10) Patent No.: US 12,035,881 B2
(45) Date of Patent: Jul. 16, 2024

(54) SYSTEMS AND METHODS FOR RESPONSIVE INSERTION AND RETRACTION OF ROBOTIC ENDOSCOPE

(71) Applicant: Noah Medical Corporation, San Carlos, CA (US)

(72) Inventors: Piotr Robert Slawinski, Sunnyvale, CA (US); Maziyar Keshtgar, San Bruno, CA (US); Sahba Aghajani Pedram, Los Angeles, CA (US)

(73) Assignee: NOAH MEDICAL CORPORATION, San Carlos, CA (US)

( * ) Notice: Subject to any disclaimer, the term of this patent is extended or adjusted under 35 U.S.C. 154(b) by 0 days.

(21) Appl. No.: 18/361,446

(22) Filed: Jul. 28, 2023

(65) Prior Publication Data

US 2023/0380662 A1  Nov. 30, 2023

Related U.S. Application Data

(63) Continuation of application No. PCT/US2023/016286, filed on Mar. 24, 2023.
(Continued)

(51) Int. Cl.
*A61B 1/00* (2006.01)
*A61B 1/005* (2006.01)
(Continued)

(52) U.S. Cl.
CPC ...... *A61B 1/00055* (2013.01); *A61B 1/00006* (2013.01); *A61B 1/00097* (2022.02);
(Continued)

(58) Field of Classification Search
CPC ............ A61B 1/00055; A61B 1/00097; A61B 1/00006; A61B 1/016; A61B 1/0051; A61B 1/05; A61B 1/00147; A61B 1/04; A61B 1/00009; A61B 1/2676; A61B 2034/301; A61B 34/20; A61B 34/30; A62B 5/062
(Continued)

(56) References Cited

U.S. PATENT DOCUMENTS

2008/0161681 A1*  7/2008  Hauck ............... A61B 5/063
                                                 600/424
2012/0123441 A1   5/2012  Au et al.
(Continued)

FOREIGN PATENT DOCUMENTS

WO  WO-2023192129 A1   10/2023

OTHER PUBLICATIONS

PCT/US2023/016286 International Search Report and Written Opinion dated Jul. 3, 2023.

*Primary Examiner* — Timothy J Neal
*Assistant Examiner* — James Edward Boice
(74) *Attorney, Agent, or Firm* — Wilson Sonsini Goodrich & Rosati

(57) ABSTRACT

A method is provided for controlling a tip velocity of an articulating flexible endoscope. The method comprises: generating a command to move a tip of an elongated member of the articulating flexible endoscope at an expected velocity; receiving sensor data acquired by a sensor disposed at a distal tip portion of the elongated member to calculate a tip velocity; calculate a disparity between the expected velocity and the tip velocity; and controlling the tip velocity based on the disparity.

19 Claims, 22 Drawing Sheets

Related U.S. Application Data

(60) Provisional application No. 63/480,502, filed on Jan. 18, 2023, provisional application No. 63/324,746, filed on Mar. 29, 2022.

(51) Int. Cl.
  *A61B 1/05* (2006.01)
  *A61B 5/06* (2006.01)
  *A61B 34/30* (2016.01)

(52) U.S. Cl.
  CPC .......... *A61B 1/0016* (2013.01); *A61B 1/0051* (2013.01); *A61B 1/05* (2013.01); *A61B 5/062* (2013.01); *A61B 2034/301* (2016.02)

(58) Field of Classification Search
  USPC ................................................ 600/103, 117
  See application file for complete search history.

(56) References Cited

U.S. PATENT DOCUMENTS

| | | | |
|---|---|---|---|
| 2012/0203065 A1* | 8/2012 | Higgins | G16H 50/30 600/117 |
| 2014/0148808 A1* | 5/2014 | Inkpen | A61B 90/06 73/866.5 |
| 2017/0280978 A1 | 10/2017 | Yamamoto et al. | |
| 2018/0177383 A1 | 6/2018 | Noonan et al. | |
| 2019/0183585 A1* | 6/2019 | Rafii-Tari | A61B 34/20 |
| 2019/0239723 A1 | 8/2019 | Duindam | A61B 1/0016 |
| 2019/0320874 A1* | 10/2019 | Yu | H02P 21/18 |
| 2019/0328207 A1 | 10/2019 | Ueda et al. | |
| 2019/0365209 A1* | 12/2019 | Ye | G06T 7/55 |
| 2019/0365479 A1 | 12/2019 | Rafii-Tari | |
| 2022/0250242 A1* | 8/2022 | Suresh | B25J 9/1689 |

* cited by examiner

SYSTEMS AND METHODS FOR RESPONSIVE INSERTION AND RETRACTION OF ROBOTIC ENDOSCOPE

REFERENCE

This application is a continuation of International Application No. PCT/US2023/016286, filed Mar. 24, 2023, which claims priority to U.S. Provisional Patent Application No. 63/324,746, filed on Mar. 29, 2022, and U.S. Provisional Patent Application No. 63/480,502, filed on Jan. 18, 2023, each of which is entirely incorporated herein by reference.

BACKGROUND

Endoscopy procedures use an endoscope to examine the interior of a hollow organ or cavity of the body. Unlike many other medical imaging techniques, endoscopes are inserted into the organ directly. Flexible endoscope that can deliver instinctive steering and control is useful in diagnosing and treating diseases that are accessible through any natural orifice in the body. Depending on the clinical indication, the endoscope may be designated as bronchoscope, ureteroscope, colonoscope, gastroscope, ENT scope, and various others. For example, flexible bronchoscope may be used for lung cancer diagnosis and/or surgical treatment. However, one challenge in bronchoscopy is reaching the upper lobe of the lung while navigating through the airways. In another example, flexible endoscopy has been used to inspect and treat disorders of the gastrointestinal (GI) tract without the need for creating an opening on the patient's body. The endoscope is introduced via the mouth or anus into the upper or lower GI tracts respectively. A miniature camera at the distal end captures images of the GI wall that help the clinician in their diagnosis of the GI diseases. Simple surgical procedures (like polypectomy and biopsy) can be performed by introducing a flexible tool via a working channel to reach the site of interest at the distal end.

Endoscopes are traditionally made to be re-usable, which may require thorough cleaning, dis-infection, and/or sterilization after each procedure. In most cases, cleaning, dis-infection, and sterilization may be aggressive processes to kill germs and/or bacteria. Such procedures may also be harsh on the endoscopes themselves. Therefore, the designs of such re-usable endoscopes can often be complicated, especially to ensure that the endoscopes can survive such harsh cleaning, dis-infection, and sterilization protocols. Periodical maintenance and repairs for such re-usable endoscopes may often be needed.

Low cost, disposable medical devices designated for a single-use have become popular for instruments that are difficult to clean properly. Single-use, disposable devices may be packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. Traditional endoscopes often include a handle that operators use to maneuver the endoscope. For single-use endoscopes, the handle usually encloses the camera, expensive electronics, and mechanical structures at proximal end in order to transmit the video and allow the users to maneuver the endoscope via a user interface. This may lead to high cost of the handle for a single-use endoscope.

Continuum robots and endoscopes are usually long and flexible. The shafts of the endoscope may suffer from a limitation of buckling or kink on insertion of the devices into the anatomy. The passive deformation of the endoscope shaft may be the result of insertion forces as well as contact with the anatomy which deformation is difficult to model. The prolapse or kink may result in potential damage as it may expose the sharp edges of the kinked elongate device and complicate the surgical procedure. Moreover, a bent or kinked elongate device may render the system losing location/shape control of the device and it may block the passage of an instrument.

SUMMARY OF THE INVENTION

Recognized herein is a need for a robotic endoscope that allows for performing surgical procedures or diagnostic operations with improved performance and cost-efficiency. Recognized also herein are devices and systems comprising endoscopes which may be disposable and may not require extensive cleaning procedures. The present disclosure provides low-cost, single-use articulatable endoscope for diagnosis and treatment in various applications such as bronchoscopy, urology, gynecology, arthroscopy, orthopedics, ENT, gastro-intestine endoscopy, neurosurgery, colonoscopy, and various others. In some embodiments, the present disclosure provides a single-use, disposable, robotically controlled bronchoscope for use with a robotic system to enable diagnostic evaluation of lesions anywhere in the pulmonary anatomy. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In an aspect of the present disclosure, a method is provided for controlling a tip velocity of an articulating flexible endoscope. The method comprises: generating a command to move a tip of an elongated member of the articulating flexible endoscope at an expected velocity; receiving sensor data acquired by a sensor disposed at a distal tip portion of the elongated member to calculate a tip velocity; calculate a disparity between the expected velocity and the tip velocity; and controlling the tip velocity based on the disparity.

In an aspect, a method for controlling a tip motion of an articulating flexible endoscope is provided. The method comprises: generating a command to drive an elongated member of the articulating flexible endoscope along an anatomical pathway via an instrument driving mechanism (IDM); receiving sensor data acquired by a position sensor disposed at a distal tip portion of the elongated member; upon determining the distal tip portion is at a pre-selected location within the anatomical pathway, setting a motion of the distal tip to zero and calculating the motion of the distal tip portion within a time window; calculating a disparity between the motion of the distal tip portion and a motion of the IDM within the same time window; and detecting a buckling event by comparing the disparity to a threshold.

In some embodiments, the pre-selected location is main carina. In some embodiments, the method further comprises determining the distal tip portion is at the pre-selected location based at least in part on the sensor data and a 3D model of the anatomical pathway. In some cases, the position sensor comprises an electromagnetic sensor.

In some embodiments, the method further comprises determining the distal tip portion is at the preselected location based at least in part on image data acquired by a camera located at the distal tip portion. In some embodiments, the threshold is determined dynamically based on a target anatomical region the articulating flexible endoscope is moving towards. In some embodiments, the threshold is a function of a tortuosity of the anatomical pathway.

In some embodiments, a size of the time window is between four seconds to eight seconds. In some cases, the size of the time window is determined based on empirical data. In some embodiments, the motion of the distal tip portion within the time window is an accumulation of distance traveled at each time step.

In some embodiments, the method further comprises setting an insertion force applied by the IDM to zero upon determining the distal tip portion is at the pre-selected location within the anatomical pathway and comparing the insertion force with a force threshold. In some embodiments, the method further comprises generating and displaying a warning message on a user interface upon determining the insertion force is above the force threshold.

In some embodiments, the method further comprises controlling a velocity of the distal tip portion of the elongated member based on a disparity between an expected velocity and a measured tip velocity. In some cases, the measured tip velocity is calculated as a filtered time derivative of the sensor data projected in a heading direction. In some cases, the expected velocity is based on an input command. In some instances, controlling a velocity of the distal tip portion of the elongated member comprises a closed loop control. For example, the measured tip velocity is processed by a low-pass filter to be utilized a feedback signal for the closed loop control.

In some embodiments, the distal tip portion comprises a structure to receive an imaging device, the position sensor, and an illumination device. In some embodiments, a proximal end of the elongated member of the articulating flexible endoscope is connected to IDM for applying a force to one or more pull wires for articulating the distal tip portion of the elongated member, inserting or retracting the articulating flexible endoscope. In some embodiments, the method further comprises displaying, on a user interface, a message indicative of the buckling event and a recommendation for taking an action in response to the buckling event.

In a related yet separate aspect, a system for controlling a tip motion of an articulating flexible endoscope is provided. The system comprises: a memory storing computer-executable instructions; one or more processors in communication with the articulating flexible endoscope and configured to execute the computer-executable instructions to: generate a command to drive an elongated member of the articulating flexible endoscope along an anatomical pathway via an instrument driving mechanism (IDM); receive sensor data acquired by a position sensor disposed at a distal tip portion of the elongated member; upon determining the distal tip portion is at a pre-selected location within the anatomical pathway, set a motion of the distal tip to zero and calculate the motion of the distal tip portion within a time window; calculate a disparity between the motion of the distal tip portion and a motion of the IDM within the same time window; and detect a buckling event by comparing the disparity to a threshold.

It should be noted that the provided modular endoscope components and various components of the device can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Figure 1:
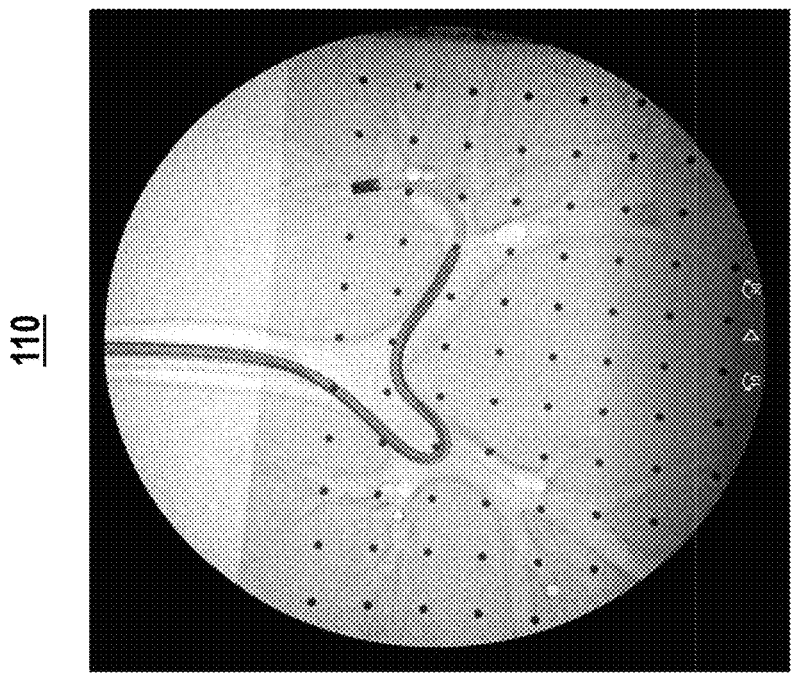
FIG. 1 schematically shows an example of a luminal network of a patient.
Figure 1:
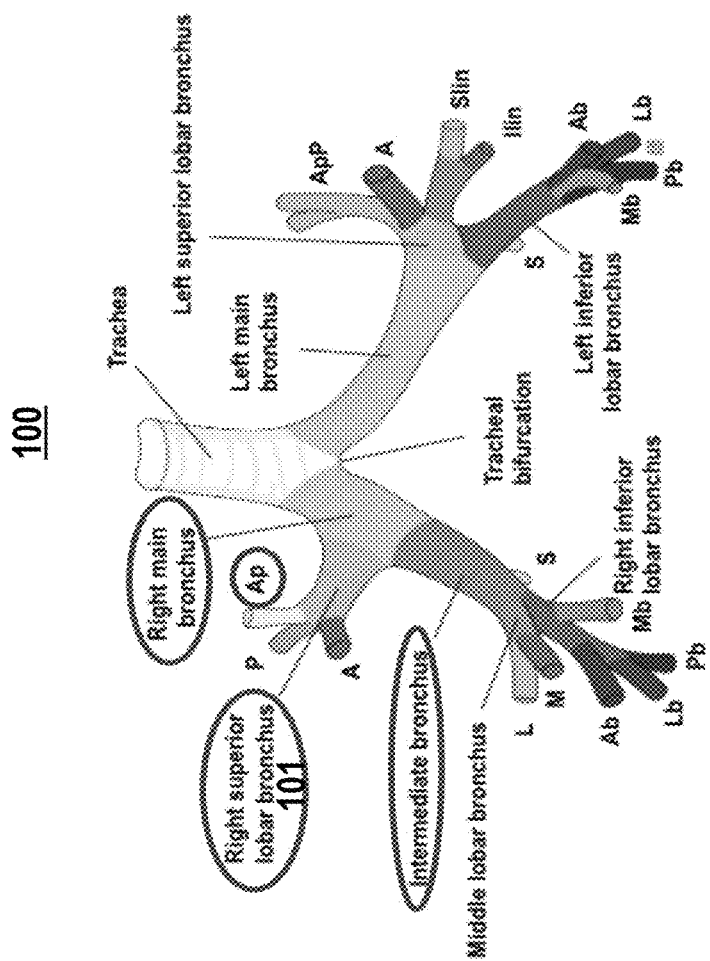

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

While exemplary embodiments will be primarily directed at a device or system for bronchoscopy, one of skill in the art will appreciate that this is not intended to be limiting, and the devices described herein may be used for other therapeutic or diagnostic procedures and in various anatomical regions of a patient's body. The provided device or system can be utilized in urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat, and various others, in the forms of. NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

The systems and apparatuses herein can be combined in one or more of many ways to provide improved diagnosis and therapy to a patient. Systems and apparatuses provided herein can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of a primary shaft or catheter may correspond to a proximal location of an elongate member of the patient, and a proximal location of the primary sheath or catheter may correspond to a distal location of the elongate member of the patient.

Responsive Insertion and Retraction Control

As described above, one challenge in navigating endoluminal device (e.g., bronchoscopy) is reaching the hard to reach regions (e.g., upper lobe of the lung) while navigating through the airways. FIG. 1 schematically shows an example of a luminal network 100 of a patient. In the illustrated embodiment, the luminal network 100 is a bronchial network of airways (i.e., lumens, branches) of the patient's lung. Although the illustrated luminal network 100 is a bronchial network of airways within the patient's lung, this disclosure is not limited to only the illustrated example. Systems and methods described herein may be used to navigate any type of luminal network, such as bronchial networks, renal networks, cardiovascular networks (e.g., arteries and veins), gastrointestinal tracts, urinary tracts, as described elsewhere herein.

Access to the peripheries of the right upper lobe 101 of the lung through the Apical segment (Ap) has been a challenge with conventional bronchoscopes. In the example 110 shown in FIG. 1, the sharp 180-degree angle between trachea and Ap combined with the large space at the junction of intermediate bronchus, right main bronchus, and the right upper lobar bronchus may cause bronchoscopes to kink and/or prolapse downward through the intermediate bronchus. As sections of elongate device are curved as they are moved through the one or more passageways, the curved sections are subject to compression. The compression causes the elongate device to bend and contact the walls of one or more passageways along its length. In areas where there are one or more large passageways around the elongate device, when the distal end of the device encounters tissue resistance, the elongate device may bend within the large airway and move towards an unintended region of anatomy and not in the intended direction ("prolapsing"). Prolapsing is more probable when tissue resistance gets higher (e.g., due to airways being too small, lung not fully inflated, diseased tissue, blind insertion, etc.). The example 110 shows that deflection/kinking of the shaft of the scope can even deflect into the opposing side bronchus (e.g., when the tip cannot move forward, but the operator continues to try and drive the scope further).

Figure 2:
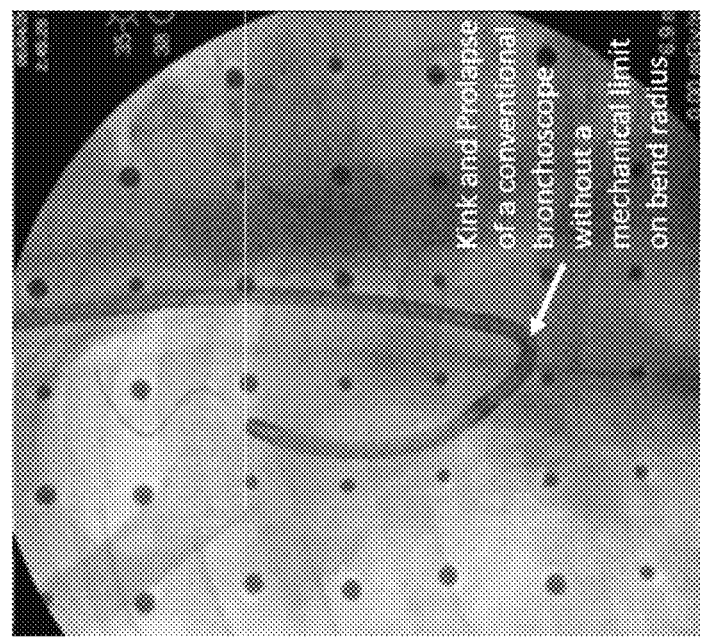
FIG. 2 shows an example of a flexible elongate member navigated through an airway/channel experiencing proposing and buckling.
Figure 2:
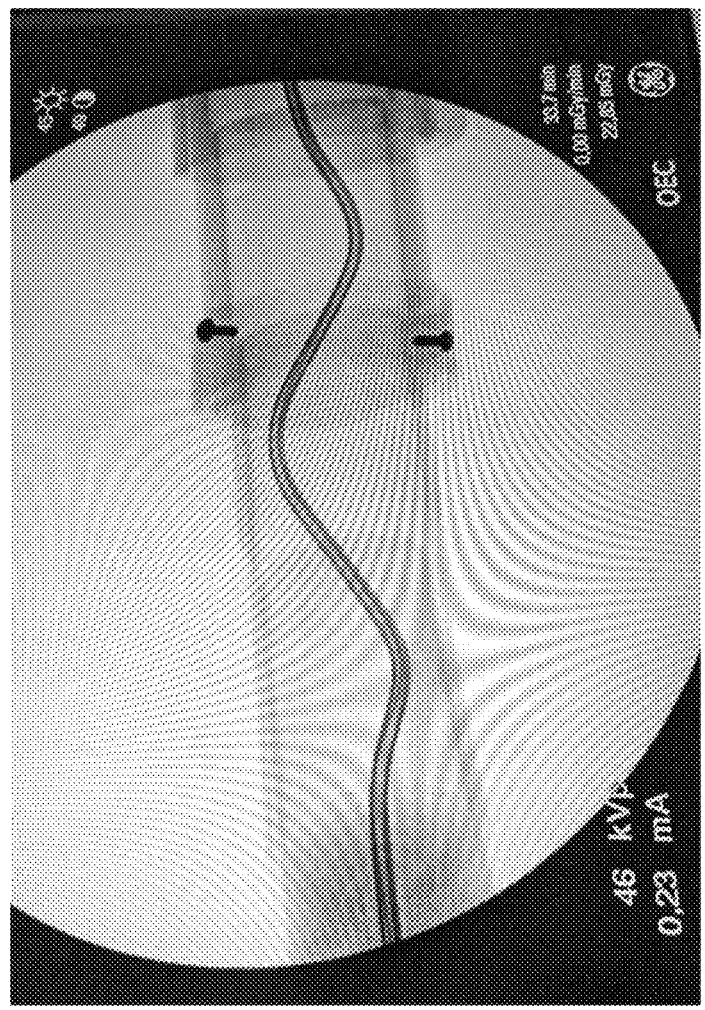

FIG. 2 shows examples of prolapsing 210 and buckling 220 during insertion of a flexible device. When the flexible endoscope is pushed at the proximal end, during insertion of the flexible device into the anatomy, the flexible endoscope may deform 210 when navigating through turns and buckling 220. The deformation may happen during insertion, as the flexible device may take on a minimum-energy shape, which may be a "hugging" of the shaft against tissue. The buckling may happen when resistance force is encountered in the distal portion of the shaft.

Figure 3:
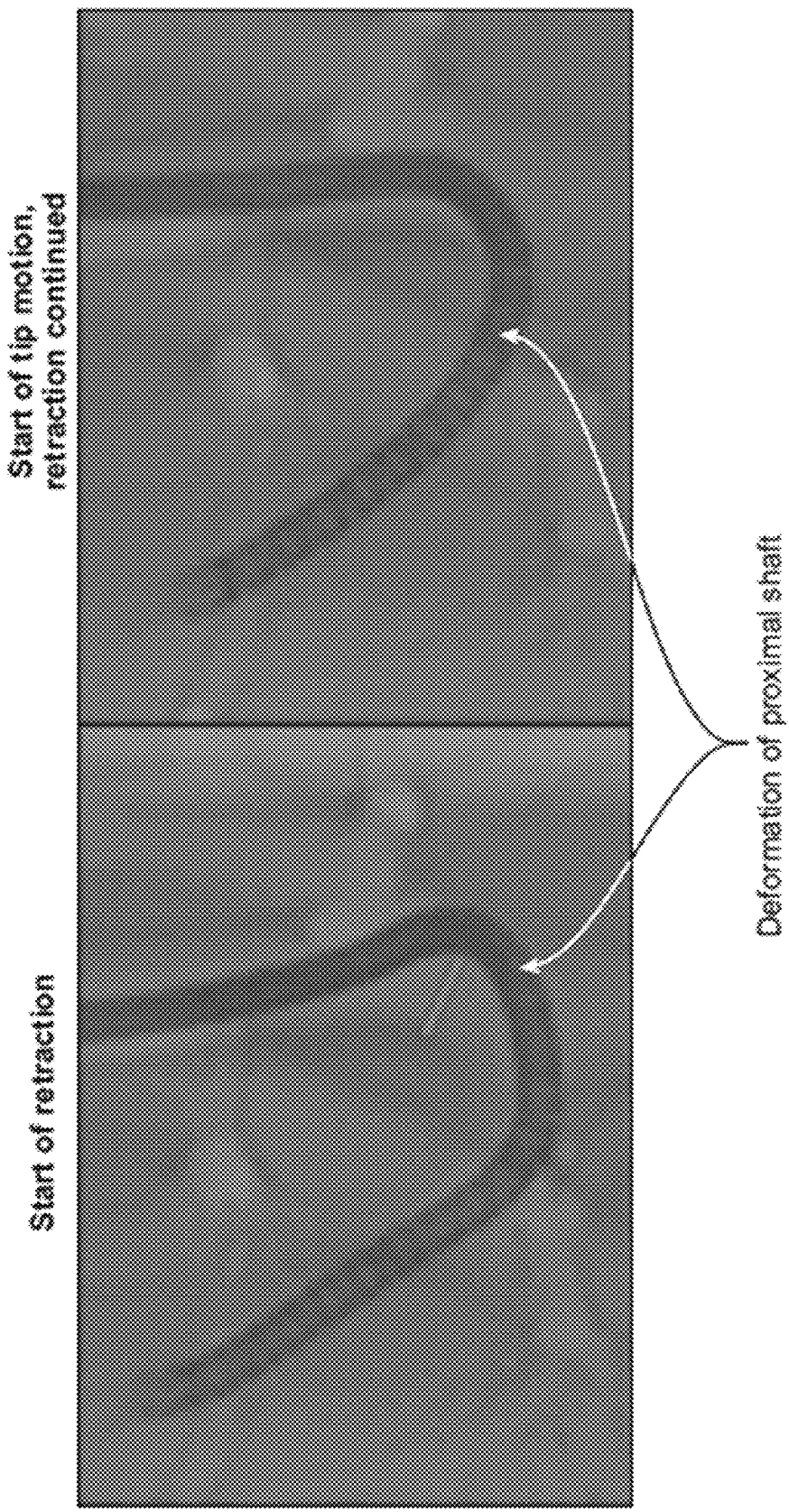
FIG. 3 shows an example of a dead-zone occurred during controlling the retraction of an endoscope.

During retraction of the flexible device, the distance of the shaft that is "lost to buckling" may become slack when the system actuation direction is reversed. This phenomenon will result in a perceived dead-zone or system delay. For example, a user's input to command movement of the robotic endoscope tip does not map directly to robotic endoscope tip motion. FIG. 3 shows an example of the dead-zone in controlling the retraction of an endoscope. When an endoscope is buckled, a retraction of the endoscope may result in robotic actuation with little endoscope tip translation movement.

The prolapse or kink may result in potential damage as it may expose the sharp edges of the kinked elongate device and complicate the surgical procedure. Moreover, a bent or kinked elongate device may render the system losing location/shape control of the device during both insertion and retraction and it may block the passage of an instrument. Furthermore, a device that prolapses or kinks may not be able to provide adequate reach towards the target anatomy for performing the intended task. Current methods to solve the kink/prolapse issue may include detecting a prolapse, using shape sensing, force sensing, medical imaging of the device shape and location (compare detected location and expected location) to detect when prolapse may occur. However, such methods require additional imaging or sensing methods for determining the shape and deformation which may not be able to provide real-time control of the movement of the endoscope tip, and may further complicate the device or increase the cost.

In an aspect of the present disclosure, methods and systems for responsive insertion and retraction velocity control of flexible endoscope is provided. The velocity control method herein may automatically correct for motion differences between the endoscope tip and a velocity command (e.g., instrument driving mechanism (IDM) command). The method for controlling a tip movement of the flexible endoscope may have an integrated safety check for detecting buckling/deformation.

Unlike the conventional methods for buckling detection based on the difference in the position of the endoscope device (e.g., expected position and measure tip position), the methods and systems herein may automatically correct the buckling/deformation during insertion and retraction based on the velocity measured at an endoscope tip and a velocity control command. This beneficially avoids shape sensing or using extra imaging approaches to determine the shape or position of the endoscope device. Additionally, velocity-based insertion and retraction control allows for a more responsive buckling auto-correction with minimal delay.

Figure 4:
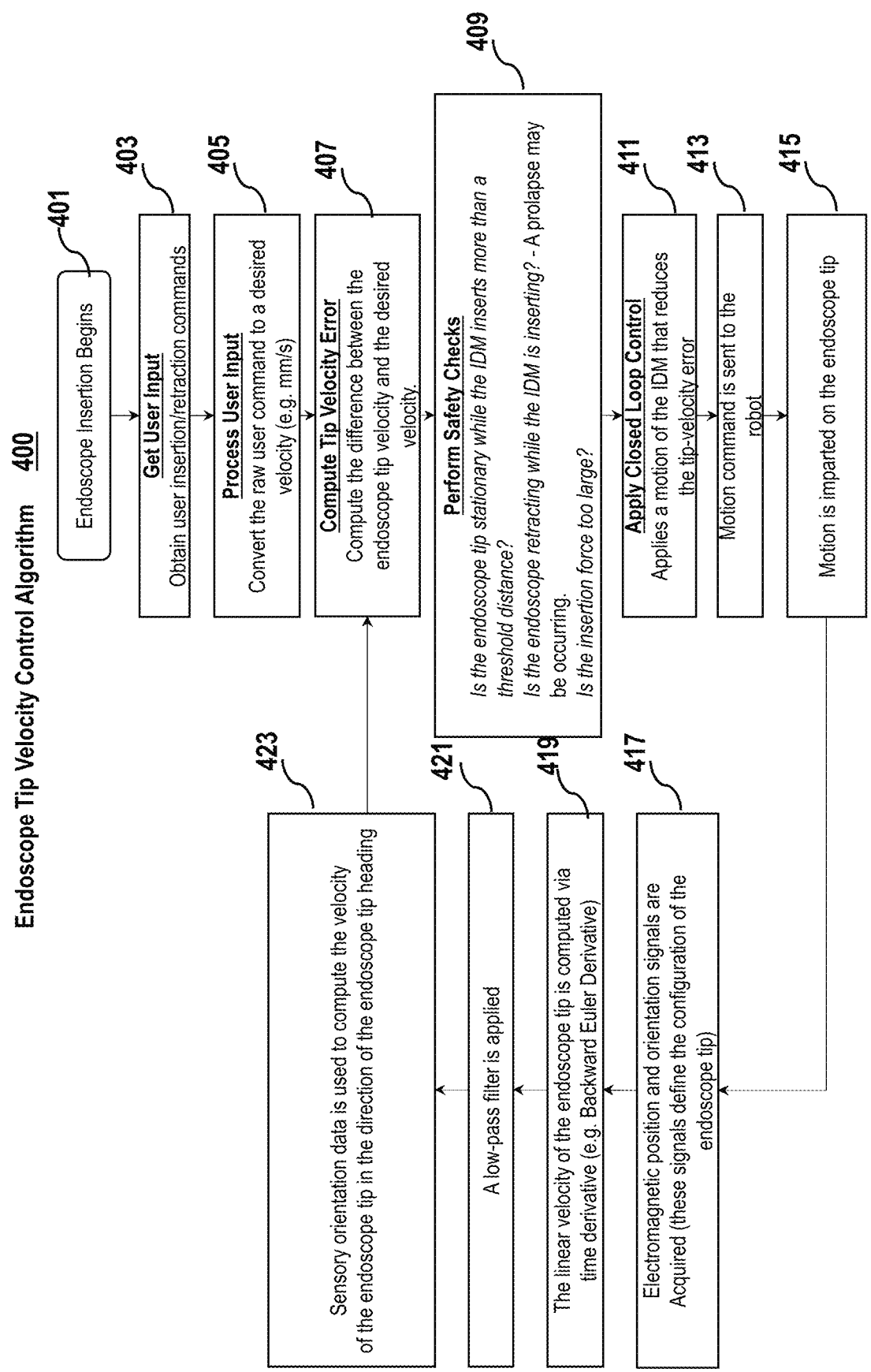
FIG. 4 shows an exemplary algorithm for controlling velocity of an endoscope tip with safety check operation, in accordance with some embodiments of the present disclosure.

FIG. 4 shows an exemplary algorithm 400 for controlling velocity of an endoscope tip with integrated safety check, in accordance with some embodiments of the present disclosure. During insertion of an endoscope device 401, a velocity command may be received by the endoscope device. The velocity command may be provided by a user input 403. For example, a user may provide a control instruction via a control interface of the endoscope device indicating a desired/expected velocity of the endoscope tip.

Figure 8:
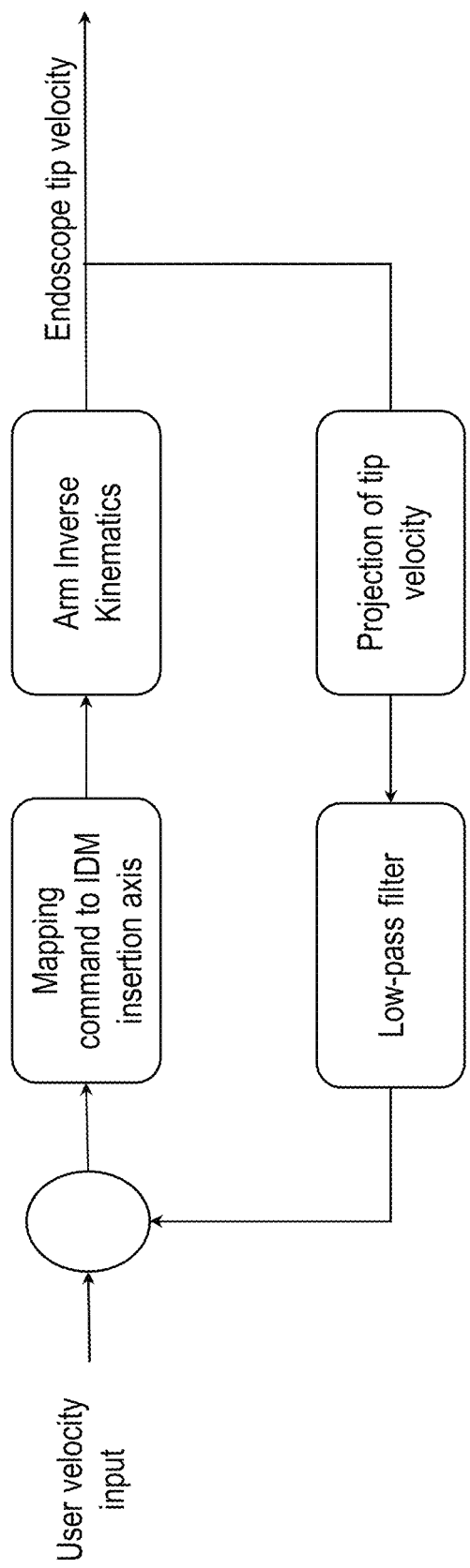
FIG. 8 shows an example of a user interface module.

The control interface of the endoscope device may be part of the user interface module for an operator or user to interact with the endoscope (e.g., bronchoscope) during surgical procedures. FIG. 8 shows an example of a user interface module 933. The user interface module may be a hand-held controller. The user interface module may, in some cases, comprise a proprietary user input device and one or more add-on elements removably coupled to an existing user device to improve user input experience. For instance, physical trackball or roller can replace or supplement the function of at least one of the virtual graphical element (e.g., navigational arrow displayed on touchpad) displayed on a graphical user interface (GUI) by giving it similar functionality to the graphical element which it replaces. Examples of user devices may include, but are not limited to, mobile devices, smartphones/cellphones, tablets, personal digital assistants (PDAs), laptop or notebook computers, desktop computers, media content players, and the like.

The user interface may include various devices such as touchscreen monitors, joysticks, keyboards and other interactive devices. A user may be able to navigate and/or control the motion of the robotic arm 911 and the motion (e.g., tip velocity) of the catheter 920 using a user input device. The user input device can have any type user interactive component, such as a button, mouse, joystick, trackball, touchpad, pen, image capturing device, motion capture device, microphone, touchscreen, hand-held wrist gimbals, exoskeletal gloves, or other user interaction system such as virtual reality systems, augmented reality systems and the like.

The user input for commanding a velocity of the endoscope tip may be received via the input device. For instance, a press on a joystick may be mapped to an analog value indicating a speed/velocity of the tip. For example, half press on the joystick may be mapped to 3 mm/s, full press may be mapped to 6 mm/s and no press may be mapped to 0 mm/s. The input velocity may be any values (e.g., continuous number) when the joystick is put in various positions.

The velocity input can be provided via any suitable user input device. In some cases, the user input device may be a tactile stylus device being physically in contact with a touch-sensitive display screen and the user may control the robotic system by moving the tactile stylus device on the display screen. For instance, one or more physical user input devices or add-on elements (e.g., trackball, joystick or roller) may be coupled to a graphical user interface (GUI) provided on a user device via tactile sense or Bluetooth. For instance, a trackball, joystick or roller may replace or supplement the function of at least one of the virtual graphical element (e.g., navigational arrow, velocity) displayed on a graphical user interface (GUI) by giving it similar functionality to the graphical element which it replaces. The add-on elements may be coupled to the GUI via a physical contact in the touch screen, via an IO port, wired or wireless communication such that the user input received via the add-on elements can be mapped to an input received by the virtual graphical elements rending on the GUI. Examples of user devices may include, but are not limited to, mobile devices, smartphones/cellphones, tablets, personal digital assistants (PDAs), laptop or notebook computers, desktop computers, media content players, and the like.

Referring back to FIG. 4, based on the specific user input device, the user input may be processed to be converted to a desired/commanded velocity of the tip of the catheter/endoscope 405. Next, a tip velocity error is computed 407. The tip velocity error is the difference between the desired/commanded tip velocity and the velocity of the endoscope tip. In some embodiments, the velocity of the endoscope tip may be measured based on sensor data. In some cases, the sensor data may comprise position and orientation information of the distal tip of the endoscope.

In some cases, the sensor signals may be acquired by positioning sensors. For example, the sensor signals may be acquired by electromagnetic coils located on the distal end used with an electromagnetic tracking system to detect the position and orientation of the distal end of the endoscope 417. For example, positioning sensors such as electromagnetic (EM) sensors may be embedded at the distal tip of the catheter and an EM field generator may be positioned next to the patient torso during procedure. The EM field generator may locate the EM sensor position in 3D space or may locate the EM sensor position and orientation in 5D or 6D space. The endoscope tip position measured by the EM sensor $p_e$=EM sensor (tip) position, may be expressed in field-generator frame.

Next, the linear velocity of the endoscope tip may be computed based on the measured location data 419. The linear velocity may be computed using time derivative method such as backward Euler derivative. In some cases, the endoscope tip velocity may be computed as the filtered time derivative of tip position (e.g., measured by the EM sensor expressed in the filed-generator frame), projected in the heading direction 423. This projection may be required because the user provided velocity command is based on integrated position changes that occur in the direction of n. The EM sensor data may be obtained at a certain frequency, such as 10-60 Hz. In some cases, a low pass filter may be applied to generate the filtered time derivative data 421.

The endoscope tip velocity may be computed as the filtered time derivative of tip position (e.g., measured by the EM sensor expressed in the filed-generator frame), projected in the heading direction of n using a projection matrix $v_n = nn^T \text{filt}(dp_e/dt)$, where n is a unit vector that indicates the endoscope tip heading direction, expressed in field-generator frame. There may be mechanical offset between the EM sensor and the scope tip and the mechanical offset may be calibrated for each endoscope device. $dp_e/dt$ represents the time derivative of the endoscope tip, $nn^T$ is the projection matrix that maps the aforementioned velocity to the heading direction of the endoscope tip (i.e. velocities that are not in the direction of the heading are ignored). The velocity $n_n$ may not be affected by articulation as the endoscope tip translation owing to articulation is orthogonal to n.

After the endoscope tip velocity is computed, the endoscope tip velocity error may be computed 407 and may be further processed for safety checks 409. In some cases, the safety checks 409 may comprise a plurality of checks. For example, the plurality of checks may comprise determining whether the endoscope tip has been stationary (e.g., tip velocity is about zero) while the handle portion of the endoscope (e.g., IDM) has an insertion distance is beyond a distance threshold. In another example, the plurality of checks may comprise determining whether the endoscope tip is retracting (e.g., negative tip velocity error) while the handle portion of the endoscope (e.g., IDM) is inserting, if yes, a prolapse may be occurring. In a further example, the plurality of checks may comprise determining whether the insertion force is beyond a force threshold. The term "insertion distance" as utilized herein may refer to the distance along the navigation path.

The method 400 may comprise a closed loop control of the tip velocity to reduce the tip velocity error 411. The tip velocity of the endoscope may be controlled based on the tip velocity error computed at operation 407 which is used as the feedback signal. FIG. 8 schematically shows a closed loop control of the tip velocity by commanding the motion of the IDM. The user velocity input may be mapped to the command to control the motion of IDM (e.g., velocity to move the IDM along the insertion axis). The command may be control signals to control the motors of the robotic arm thereby controlling a motion of the IDM (i.e., proximal end of the endoscope). The endoscope tip velocity may be calculated based on the robotic arm inverse kinematics. The endoscope tip velocity is then used to calculate the tip velocity in the heading direction by projection in the heading direction of n using a projection matrix as described above. In some cases, the feedback signal may be the projection of tip velocity processed by a low-pass filter to filter out the noise data.

Referring back to FIG. 4, based on the control algorithm, a motion command is generated to actuate the robotic arm 413 thereby affecting a tip velocity of the endoscope 415. The effect on the motion of the IDM (e.g., insertion velocity, insertion distance) and on the motion of the endoscope tip (e.g., tip velocity) may not perfectly match due to the tortuosity of the navigation path, the buckling and/or prolapse as described above.

Figure 5:
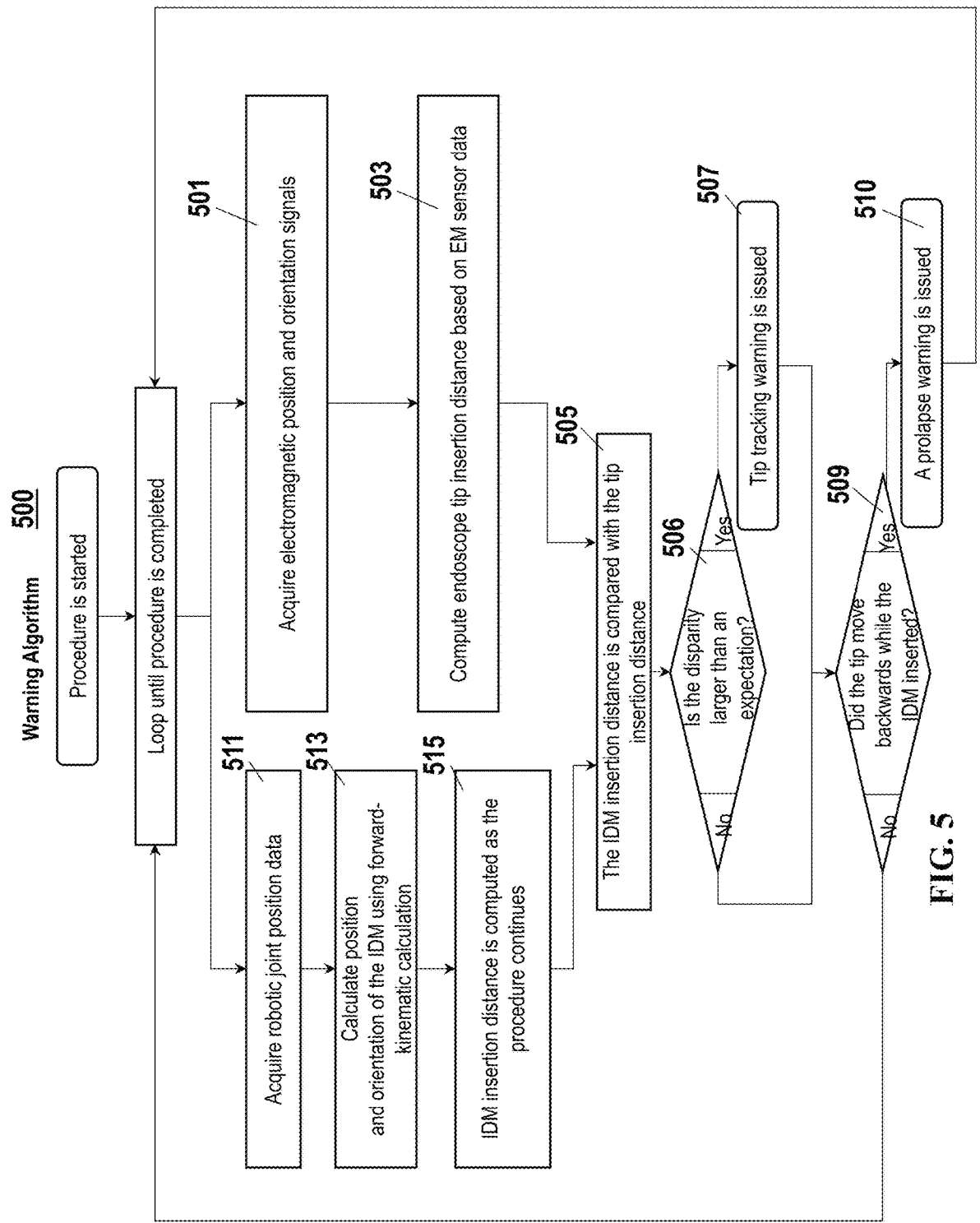
FIG. 5 shows an exemplary warning algorithm.

In some embodiments, the plurality of safety checks may be combined, ordered and selected to trigger a warning or pause of the operation according to a warning algorithm. FIG. 5 shows an exemplary warning algorithm 500. The warning algorithm may trigger operations such as warning or pause of the operation based on one or more of the plurality of safety checks. In the illustrated method, the warning may be triggered based on a comparison between the endoscope tip insertion distance and an IDM insertion distance.

The process may begin with acquiring EM sensor data (e.g., EM position and orientation signal) 501. The endoscope tip insertion distance may be computed based on the acquired EM sensor data (e.g., EM position and orientation signal) 503. For example, the endoscope tip insertion distance may be calculated based on the sensor orientation information which is used to distinguish between lateral motion and articulation, from motion that results from robotic insertion. The robotic joint position data may also be acquired 511. As described later herein, the endoscope device may be attached to a robotic arm via an IDM. The position and orientation of the IDM may be calculated based on the joint position data using forward-kinematics 513. The IDM insertion distance is computed at a series of time points 515 and is compared with the tip insertion distance 505.

Figure 6:
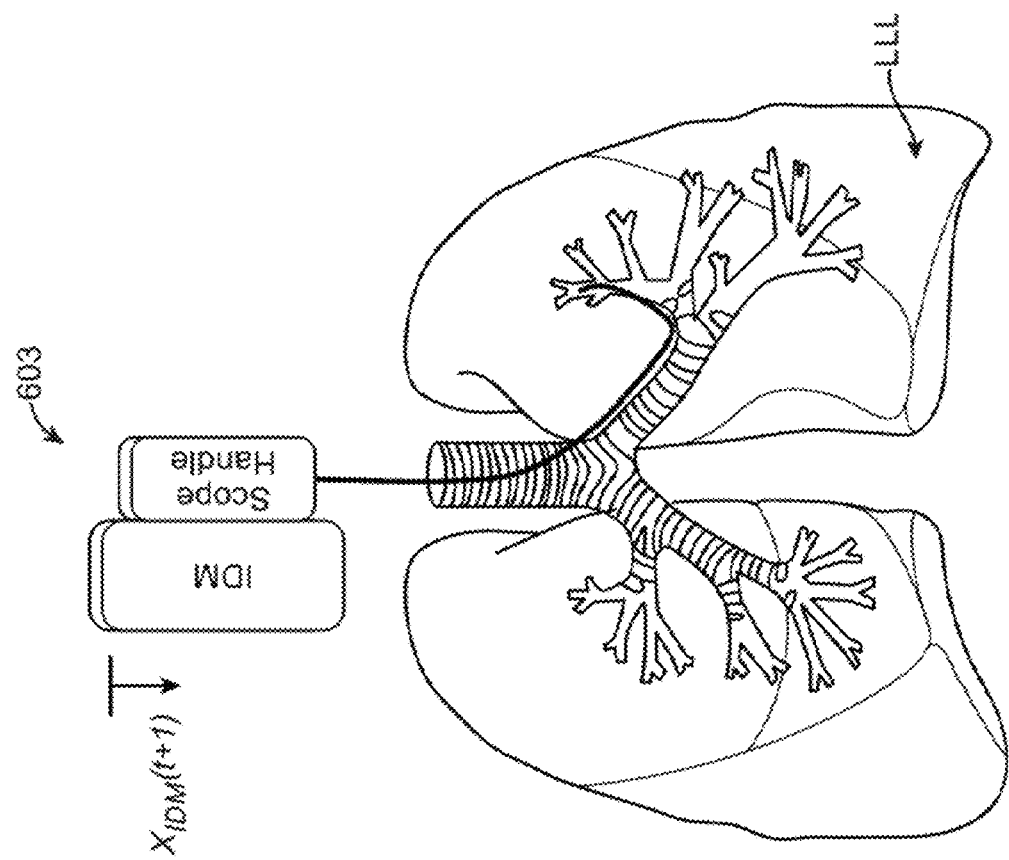
FIG. 6 shows an example of the IDM insertion distance and endoscope tip insertion distance at different time points.
Figure 6:
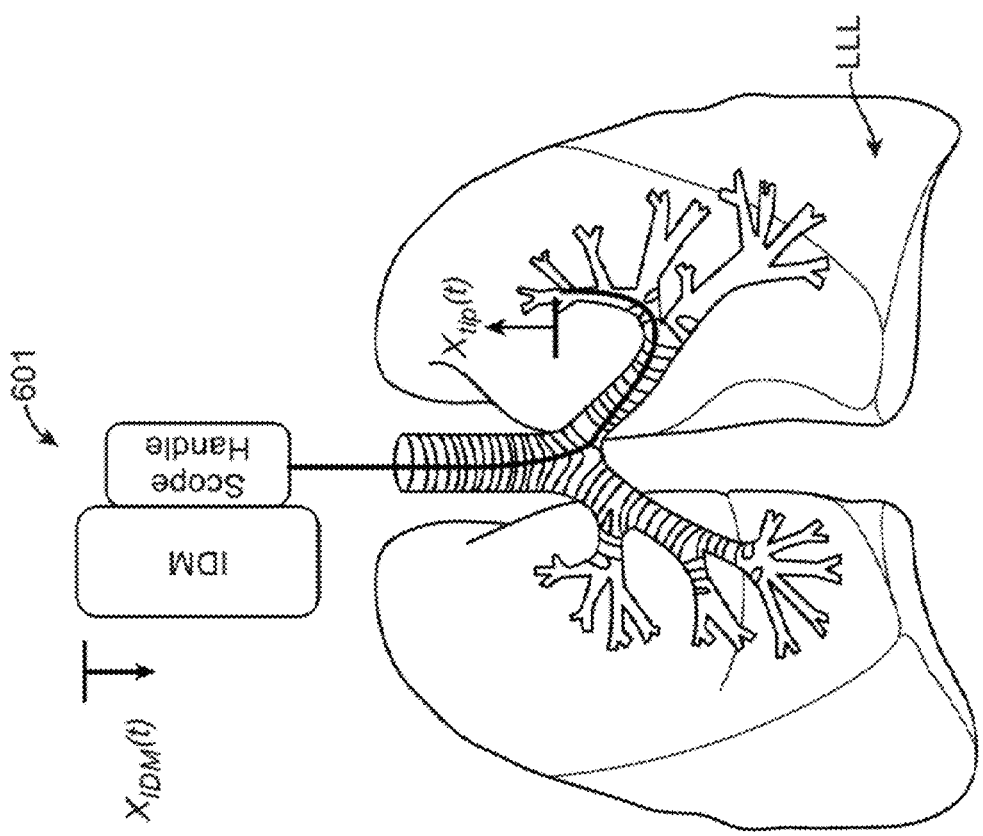

FIG. 6 shows an example of the IDM insertion distance $X_{IDM}(t)$ at time t 601 and the IDM insertion distance $X_{IDM}(t+1)$ at time t+1. The tip insertion distance is also computed as Xtip. The difference between the IDM insertion distance $X_{IDM}$ and the tip insertion distance may be the deformation loss. The deformation loss may be due to the buckling, prolapse, kink of the flexible catheter and/or the tortuosity of the navigation path. For example, a tortious path may result in greater deformation loss than navigating through a straight path.

Referring back to FIG. 5, the difference/disparity may be compared against a threshold to determine existence of buckling. The threshold may be dynamic base on one or more factors such as the anatomical region and/or tortuosity of the navigation path.

In some cases, the dynamic threshold may be referred to as dynamic tracking error threshold (DTET) which may trigger a warning and/or system safety operation when the tracking error (TE) is beyond the DTET. The tracking error may be the deformation loss as described above. As described above, the DTET may be dynamic based at least in part on the anatomical region that the flexible catheter passes through. In some cases, the DTET may be a function of the navigation path, the insertion distance or the tortuosity of the path. The tortuosity of the path may be calculated, for example, as the ratio of the length of a segment of a path to the distance between its ends.

Figure 7:
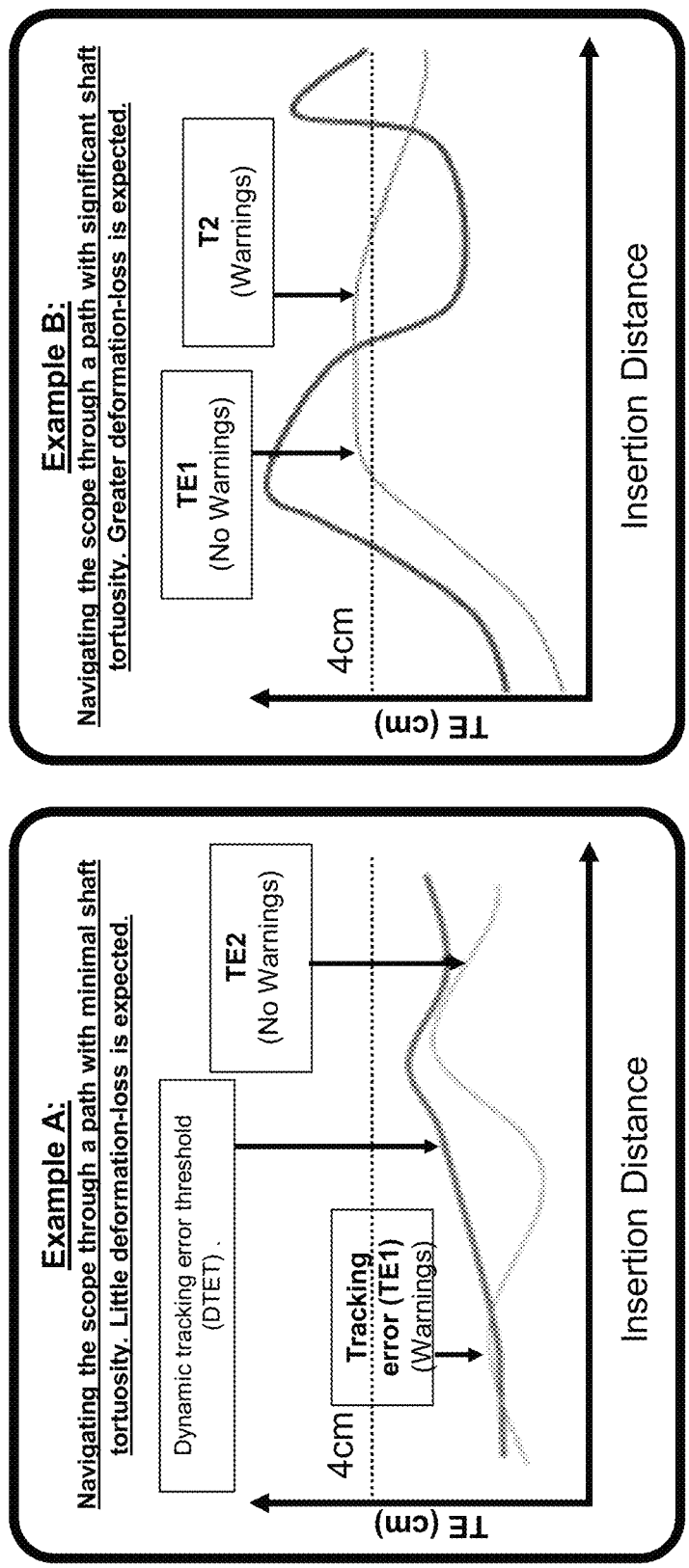
FIG. 7 shows examples of dynamic tracking error threshold (DTET) as function of the insertion distance.

FIG. 7 shows examples of dynamic tracking error threshold (DTET) as function of the insertion distance. Example A shows the DTET of a path with less tortuosity thus the overall value of the DTET is a function of the insertion distance and the maximum value is below 4 cm. The tracking error (TE) has been compared against the DTET at various insertion distances and when the TE is beyond the DTET for a given insertion distance, a warning may be triggered, e.g., TE1. Example B shows the DTET of a path with greater tortuosity thus the overall value of the DTET is a function of the insertion distance and the value is greater than 4 cm at certain insertion distance (or certain anatomical region).

During retraction of the medical device, a previously determined deformation-loss during insertion may be used as a feed-forward term to perform a backslash compensation for the retraction control. This reduces the deformation-loss incurred during the insertion prior to the tip motion during the retraction.

The dynamic tracking error threshold may be determined using any suitable method such as based on historical data, computerized tomography (CT) scans of the anatomy, 3D model of the navigation path and the like. For example, the tortuosity of the path may be calculated for various anatomical regions, segments, insertion length along the path and the DTET may be varied based on the anatomical region.

In some cases, in addition to the anatomical region, the DTET may also account for an effect of applying an insertion force within a safety range or acceptable deformation range. The safety range describes a range that the buckling doesn't damage contacting tissues or organs within the patient. Such safety range may be determined based on historical endoscope data and patient data regarding prior similar operations. Any suitable method may be utilized to determine such safety range. For example, a model may be trained using machine learning algorithm for determining the safety range. The historical endoscope data and patient data may be used to create training data set for training the model. The model may be continuously updated and improved as new sensor data are collected.

Referring back to FIG. 5, the dynamic tracking error threshold may be used to determine if the disparity triggers a tip tracking warning 507. Next, the process may proceed with determining whether the tip moves backward while the IDM is moving forward i.e., inserting 509. If yes, a prolapse may exist and a prolapse warning may be triggered 510.

The warning algorithm 500 is for illustration purpose only. It should be noted that fewer or more safety checks may be performed. For example, in addition to the prolapse and buckling detection, the algorithm may also comprise checking whether the insertion force is beyond a threshold. The insertion force may be detected by one or more force sensors coupled to a robotic arm of the surgical robotic system. When the insertion force is approaching the insertion force threshold within a predefined range or approaches the insertion force threshold, the surgical robotic system sends a visual, audio and/or tactile feedback to a user via the system GUI. For example, a warning indicating that the insertion force is close to the insertion force threshold, or approaches the insertion force threshold may be displayed on the GUI or delivered to the user using suitable UI features.

Figure 17:
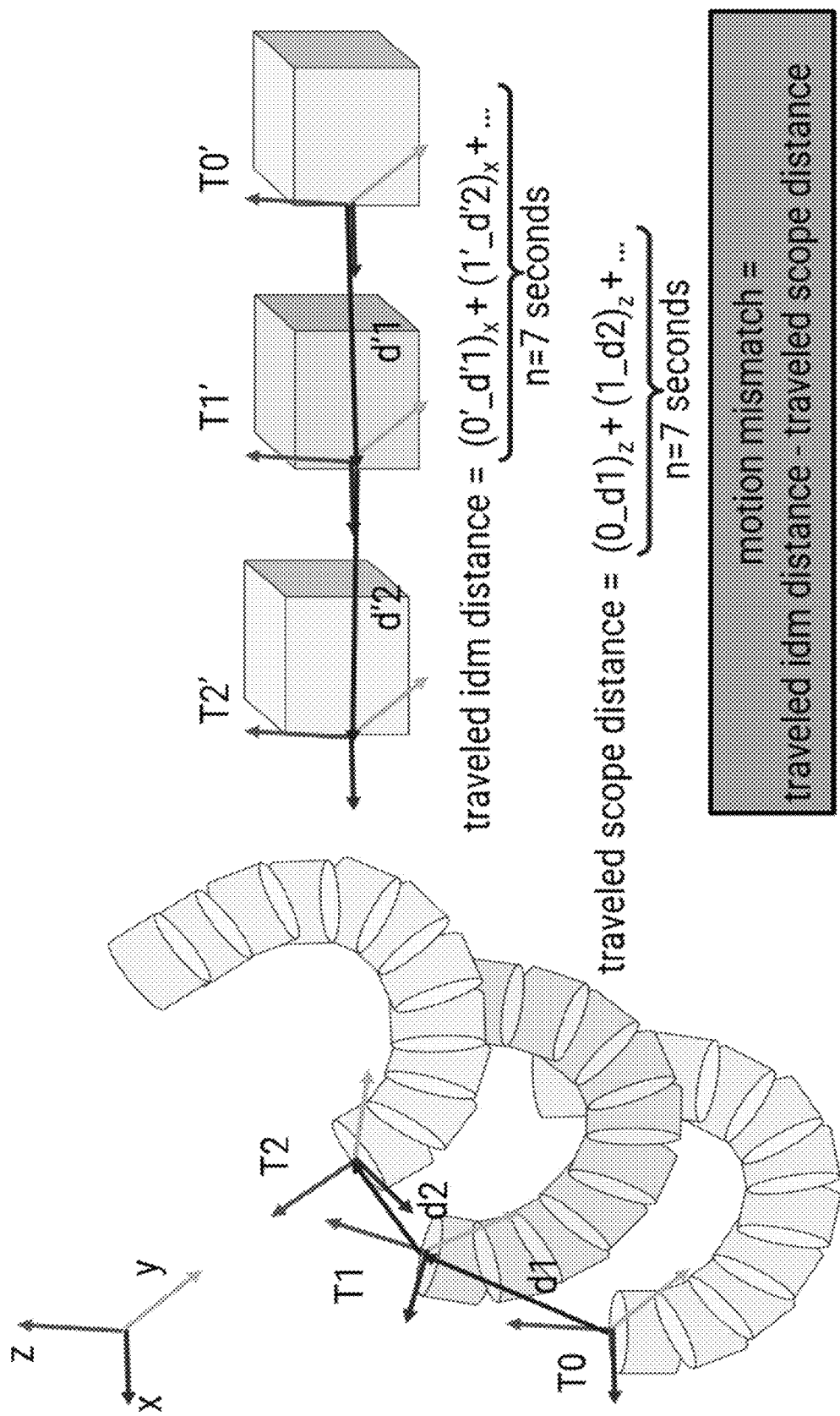
FIG. 17 shows an example of calculating a motion difference or motion mismatch within a pre-determined time window.

In some embodiments, instead of or in addition to detecting the velocity disparity, the methods herein may track the difference/disparity between the IDM insertion motion and the measured tip motion within a time window. For example, motion of the endoscope tip and the motion of the IDM may be summed up within the time window to determine a disparity. FIG. 17 shows an example of calculating a motion difference or motion mismatch within a pre-determined time window. For example, the distance traveled within each time step (e.g., d1 between $T_0$ and $T_1$, d2 between $T_1$ and $T_2$, etc.) in forward direction may be summed up for seven seconds and utilized as the total traveled distance within the time window for the endoscope tip and the IDM respectively. The motion of the endoscope tip may be measured by the EM sensor as described elsewhere herein. The EM sensor data may be obtained at a certain frequency, such as 10-60 Hz.

The motion mismatch tracked within the time window may be compared against a threshold to determine existence of buckling event. In some cases, the time window is a window of four seconds, five seconds, six seconds, seven seconds, eight seconds, a number below five seconds, greater than eight seconds or any number between the integers. The length of the time window may be selected (e.g., seven seconds) such that the motion mismatch tracked within the time window is not overly sensitive while allowing for a real-time detection of buckling event. In some cases, the size of the time window may be determined based on empirical data. In some cases, the length of time window (window size) may be adjusted based on the use application (e.g., region of the body), desired sensitivity level and the like. The length of time window may be constant throughout a procedure. Alternatively, the length of time window may vary when the endoscope is navigated to different regions in a body.

In some cases, the forward motion of the IDM and scope tip may only be tracked while the scope is commanded to be inserted using the controller. In some cases, the tracking of the motion mismatch between the IDM and the scope tip may be reset to zero if the amount of scope retraction commanded by the user exceeds a threshold value for retraction.

Figure 19:
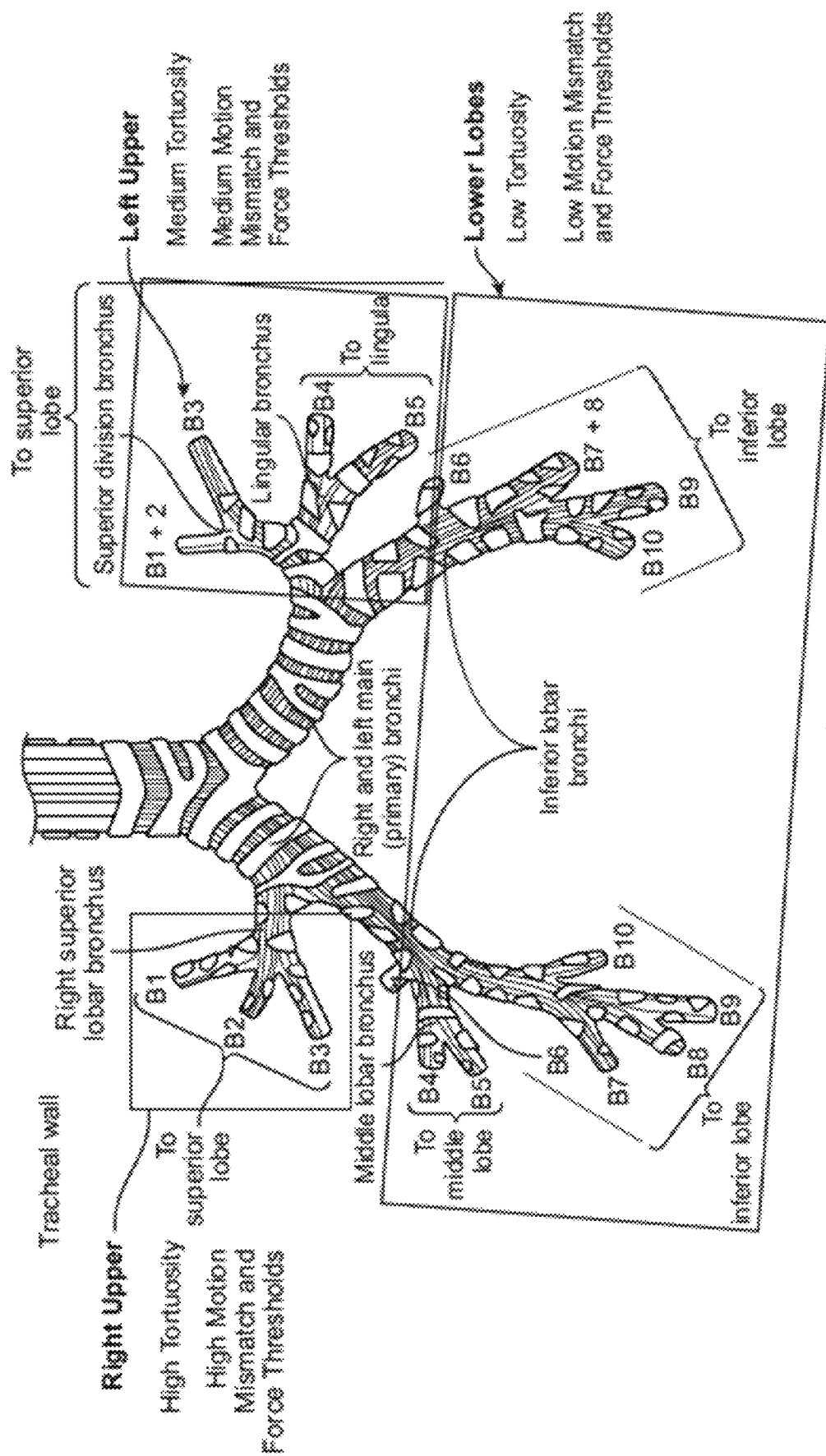
FIG. 19 shows examples of thresholds varied based on anatomical regions.

As described above, the threshold for the force and/or the threshold for the endoscope tip motion may be based on tortuosity of the path or anatomical regions. FIG. 19 shows examples of thresholds varied based on anatomical regions. In some cases, the dynamic tracking error threshold, motion mismatch threshold and/or the force threshold may be determined based on the tortuosity of the path. The amount of force exerted on anatomy by scope tip may be determined based at least in part on the force exerted by the IDM in the insertion direction and frictions between the scope and the path to the tip. Higher tortuosity may lead to higher friction thus lower force exerted on anatomy by scope tip with a fixed amount of force sensed at the IDM. FIG. 19 shows an example of different thresholds selected depending on which segment of the lung the scope drives within. For example, a higher force threshold and higher dynamic tracking error threshold/motion mismatch threshold may be selected for the right upper region due to the high tortuosity, a medium force threshold and medium level dynamic tracking error threshold may be selected for the left upper region due to the medium tortuosity and a lower force threshold and lower dynamic tracking error threshold may be selected for the lower lobes region due to the lower tortuosity. In some cases, the threshold is a function of a tortuosity of a path and the function may be determined based at least in part on an anatomical model of the subject.

Figure 16:
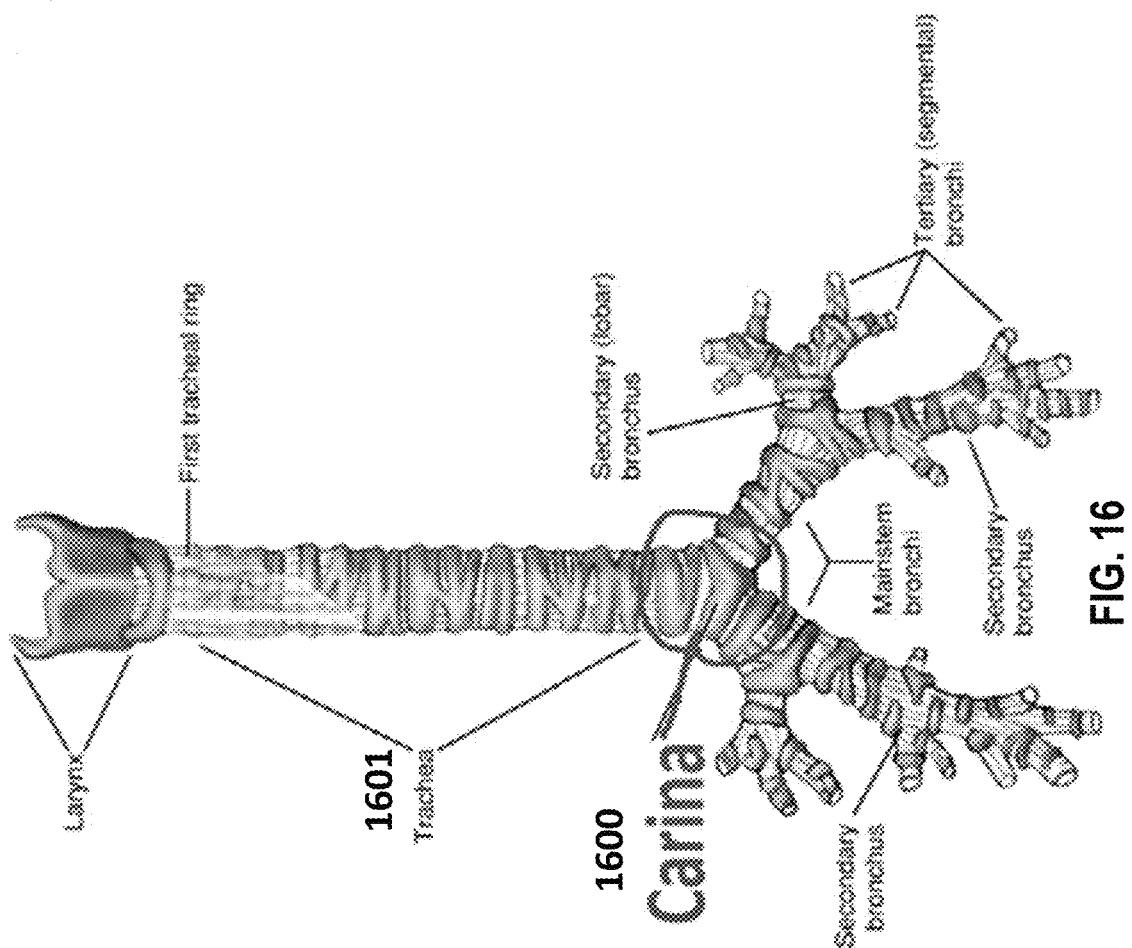
FIG. 16 shows an example of "zero position."

It can be challenging for detection utilizing thresholds (e.g., force threshold and dynamic tracking error threshold) because the amount of motion mismatch and end effector force up to the main carina of the lung can be variables affected by the initial set up. For instance, as shown in FIG. 16, the mount of motion mismatch and end effector force up to the main carina point 1600 may be dependent on variables in the setup such as the friction within the endotracheal tube, mechanical interface with the bronchus adapter, robot arm angle after retraction, scope stiffness profile, and/or different amounts of lubricants applied to the scope. The algorithms and methods herein may beneficially avoid the noise or uncertainty introduced by the initial set up conditions by setting the force and/or motion mismatch values to zero as the tip of the endoscope moves along the endotracheal tube 1601 up to the main carina 1600. It should be noted that the zero position can be selected as other suitable location such as a location within a distance from the main carina or a location depending on the anatomical structure.

In some cases, the main carina location 1600 may be pre-selected as the zero position. For example, as the endoscope is inserted through the trachea and upon reaches the main carina point 1600, the system may initiate tracking the motion mismatch starting as zero and comparing it against the motion mismatch (or dynamic tracking error threshold) as described elsewhere herein. Similarly, the force may also be set as zero when the tip of the endoscope reaches the main carina location 1600 and the system may start tracking the force and comparing it against the force threshold for detecting a safety event.

In some cases, the system may automatically set the force and/or the motion mismatch between the IDM and the endoscope tip motion to zero upon determine endoscope tip is at the main carina 1600. The systems and methods herein may detect the zero position at main carina using various suitable methods. In some case, the system may utilize the navigation data such as EM sensor data to determine whether the endoscope tip has reached the main carina. For example, by tracking the EM sensor data for tip position within the CT scanned model of the patient's lung, the system may automatically detect whether the endoscope tip has reached the main carina. In some cases, the system may employ an image recognition algorithm to detect an exit of the endoscope tip from the endotracheal tube 1601 into trachea. For example, the method may process the camera image (e.g., endoluminal view shown in FIG. 20 or FIG. 21) using the image recognition algorithm to identify the bifurcation at the main carina. Based on the detection of the bifurcation, the endoscope tip may be determined to be at the main carina 1600. Various other methods may also be utilized to automatically detect the zero position. For instance, the endoscope tip may be determined to be at the main carina location 1600 at a fixed insertion distance based on human factors after the IDM gets aligned with the Bronch Adapter and automatically retracts to the start position. The above methods for detecting the zero position can be used individually or in any combination.

Figure 18:
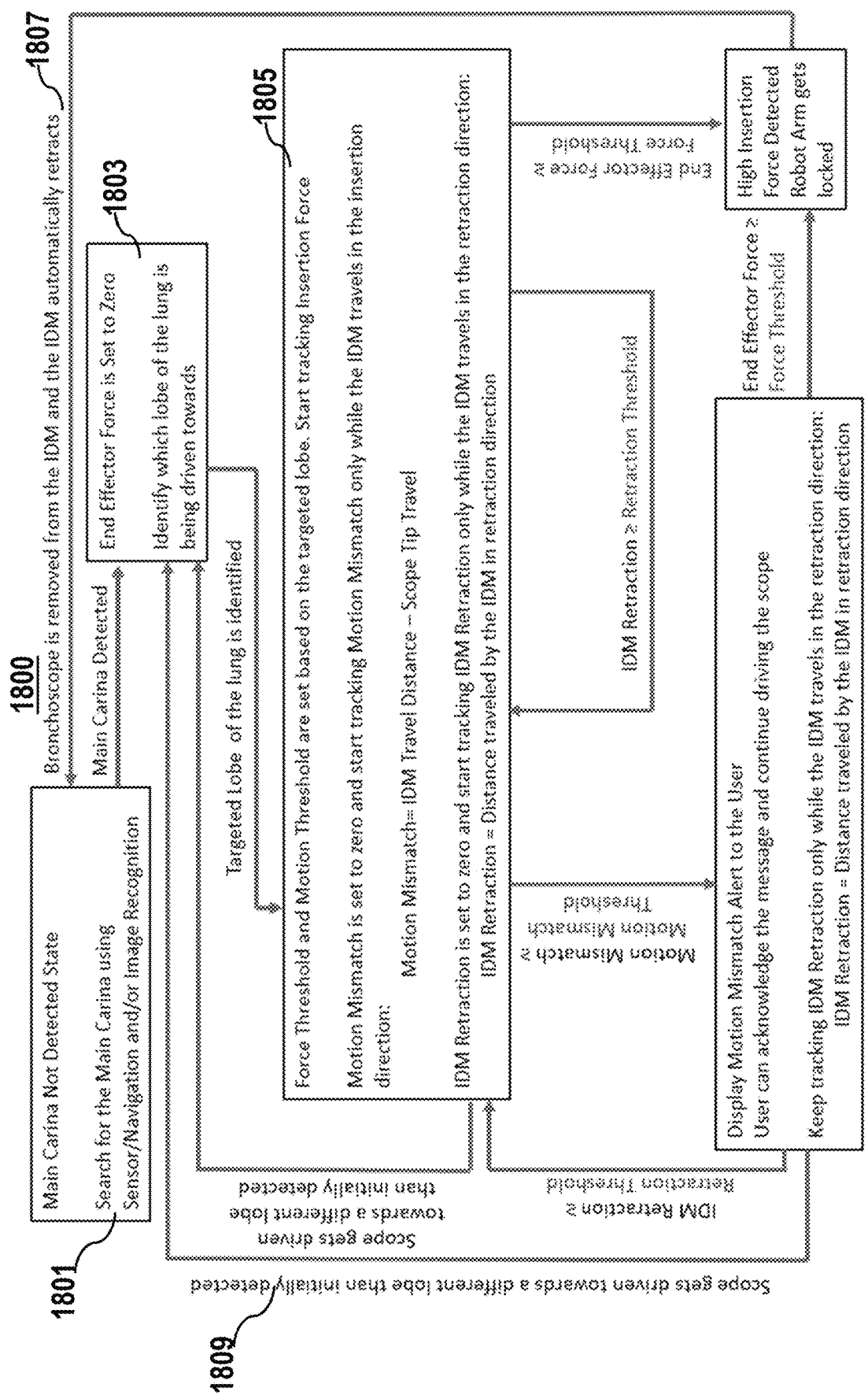
FIG. 18 shows an exemplary algorithm for controlling the endoscope tip motion.

FIG. 18 shows an exemplary algorithm 1800 for controlling the endoscope tip motion. The algorithm 1800 may begin with detecting a zero position such as the main carina 1801. The zero position may be detected using the navigation data (e.g., EM sensor data), image recognition method and/or other methods as described above. Upon detection of the zero position, the force and/or the motion mismatch for the endoscope tip may be set to zero 1803. The algorithm may also identify which lobe of the lung the endoscope is driven towards. Based on the target region, a force threshold and motion threshold (or DTET) may be determined 1805. In some cases, the algorithm may begin tracking the motion mismatch within a sliding window (e.g., window size of seven seconds) and constantly compares it against the motion mismatch threshold. For example, the sliding window may have a window size of seven seconds and the sliding size may be one second such that the comparison may be conducted every second. In some cases, the sliding size may be adjusted as one second, two seconds, three seconds and the like to adjust the detection frequency.

Upon detecting the motion mismatch is greater than the motion mismatch threshold, a warning message may be displayed on a GUI notifying a user about a possible kinking or buckling event. A user may choose to follow recommendation in the message or continue to drive the endoscope. In some cases, when the force is detected to be greater than the force threshold, a warning message may be displayed on the GUI and the robotic arm may be stopped from moving. In some cases, the warning message may provide instruction for a user to remove the endoscope and recover the system (e.g., system may automatically retract IDM) 1807. In some cases, when the endoscope is detected to be driven towards a different anatomical region (e.g., lobe) 1809, the algorithm may repeat the operation of setting the motion mismatch and force to zero 1803 and repeat the process. In the illustrated example, during retraction of the IDM/endoscope, the algorithm may track the IDM retraction distance and use the IDM retraction distance as the endoscope tip retraction distance.

Figure 20:
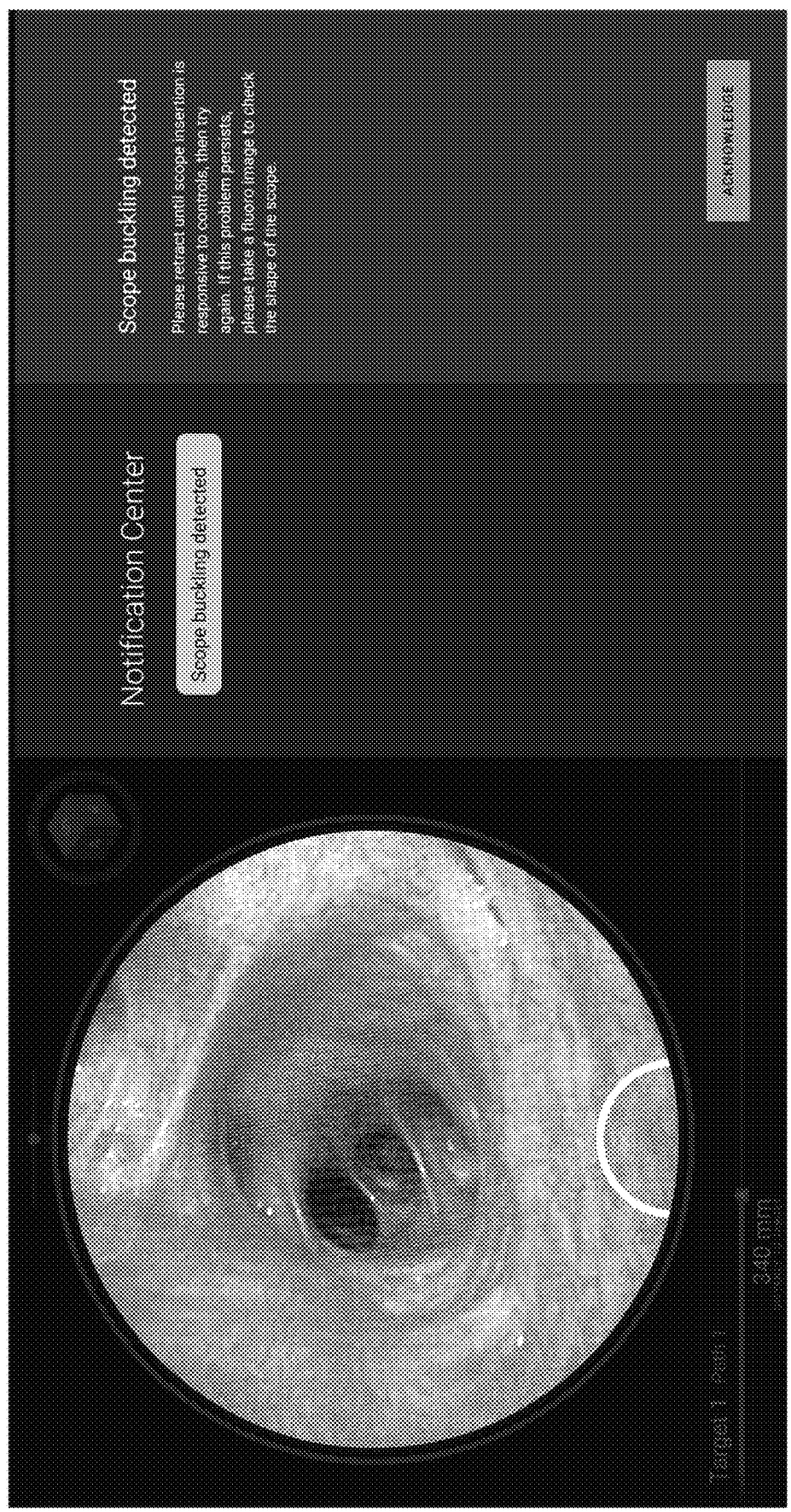
FIG. 20 and FIG. 21 show examples of GUI displaying warning messages.
Figure 21:
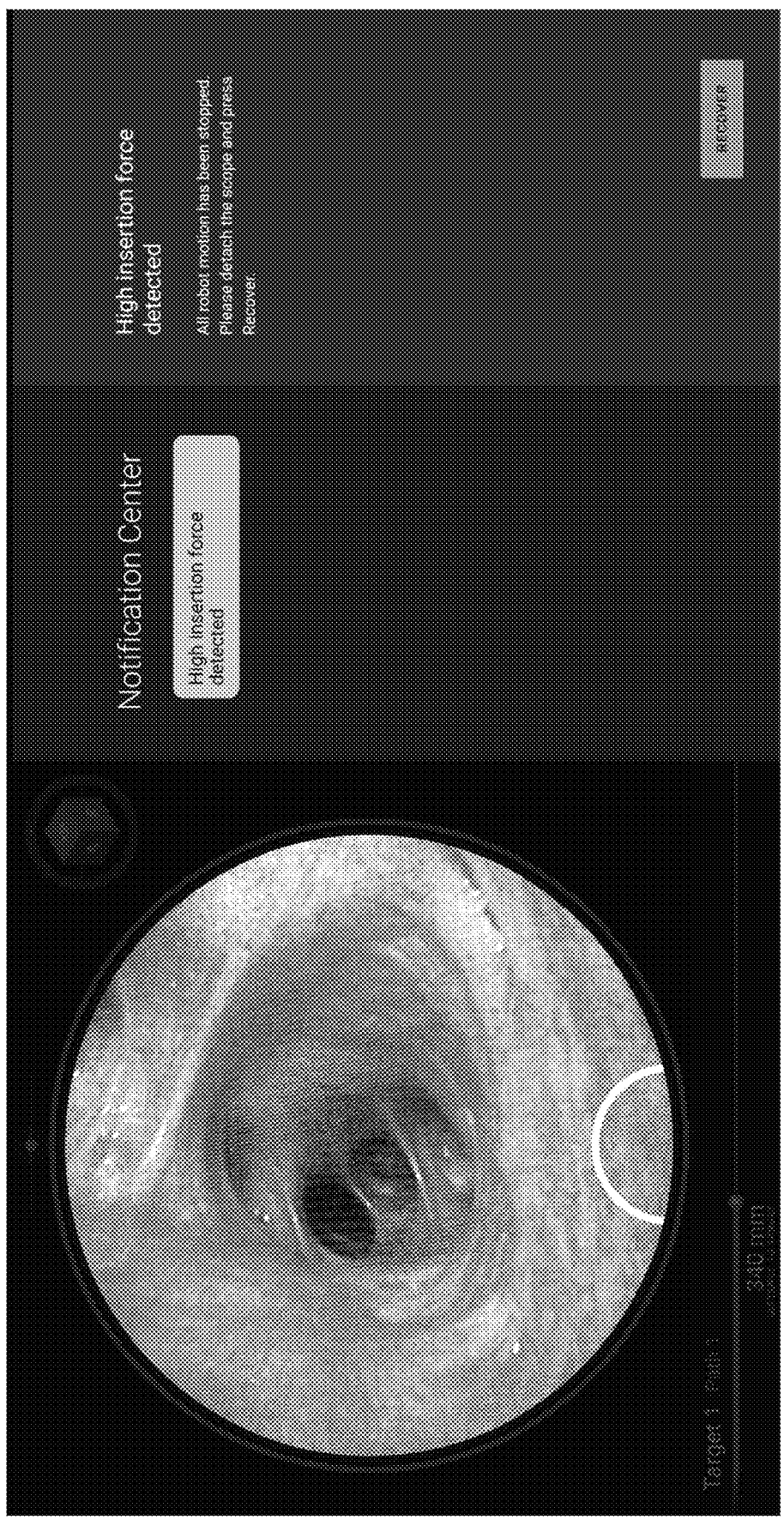

The detected buckling, prolapse, large insertion force may trigger a warning message and/or a control signal to the system. The warning or feedback message may be delivered to the user in various forms. In some cases, the warning or feedback message may indicate the type of the issue e.g., buckling, prolapse, or unsafe insertion force. For example, message or warning may be provided for display on a graphical user interface (GUI) rendered on a display being used by the operator to control the operation. In some cases, the system may also generate a recommendation for the user to take an action in response to the detected buckling event. For example, the system may generate recommendations for the user to move the endoscope backward, adjust movement of the tip, reduce/adjust the insertion force provided by the IDM, and the like. FIG. 20 shows an example of GUI displaying warning message. The notification or warning message may be displayed upon detection of scope buckling. In the illustrated example, the message may also include recommendation such as retract the scope or take a fluoroscopy image. FIG. 21 shows an example of a warning message triggered by detection of high insertion force. In the example, a warning message may be displayed on the GUI upon detecting an insertion force is beyond a force threshold. The warning message may include information that the robot motion has been stopped and recommendation to the user such as "detach the scope and press recover." In some cases, upon a user clicks the "recover" button, the system may automatically retract the IDM.

In some cases, a control signal to modify the operation of the system, the robotic arm, the IDM and/or the endoscope may be generated. For example, a control signal to adjust endoscope's movements, stop the movement of the endoscope, and like may be automatically generated based on the detection of the buckling, prolapse or great insertion force. For instance, the control signal may automatically command the actuators of the IDM and/or robotic arm to move the tip of the endoscope to reduce the buckling or insertion force. The velocity, movement and trajectory path for moving the endoscope tip may be automatically determined using an algorithm based on sensor data (e.g., EM sensor data).

Flexible Endoscope System and Device

In some embodiments, the endoscope tip velocity control methods and systems herein may be utilized for improving reliability and stability of a flexible endoscope. The provided endoscope tip velocity control mechanism may be utilized by any devices or apparatuses. In an aspect of the invention, a flexible endoscope with improved performance (e.g., improved reliability) is provided.

Figure 9:
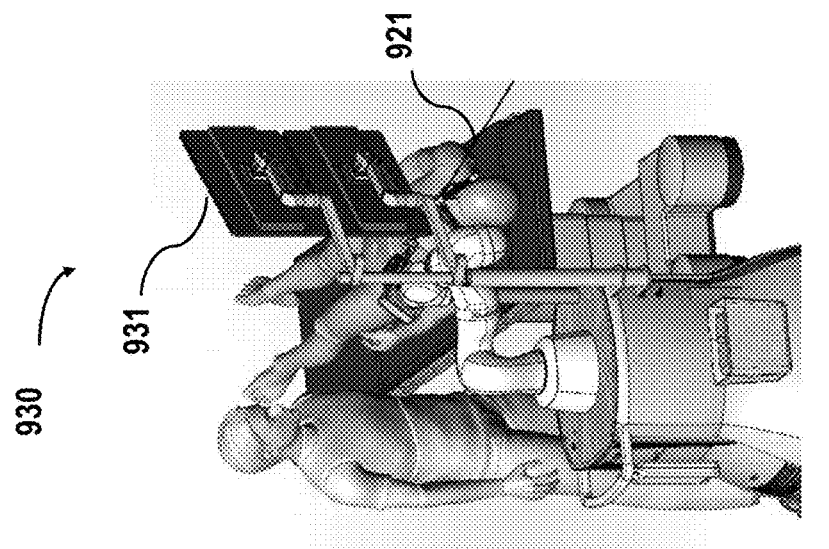
FIG. 9 show examples of a robotic endoscope (e.g., bronchoscopy) system, in accordance with some embodiments of the invention.
Figure 9:
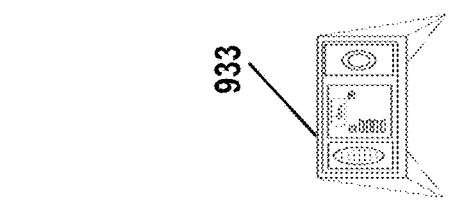
Figure 9:
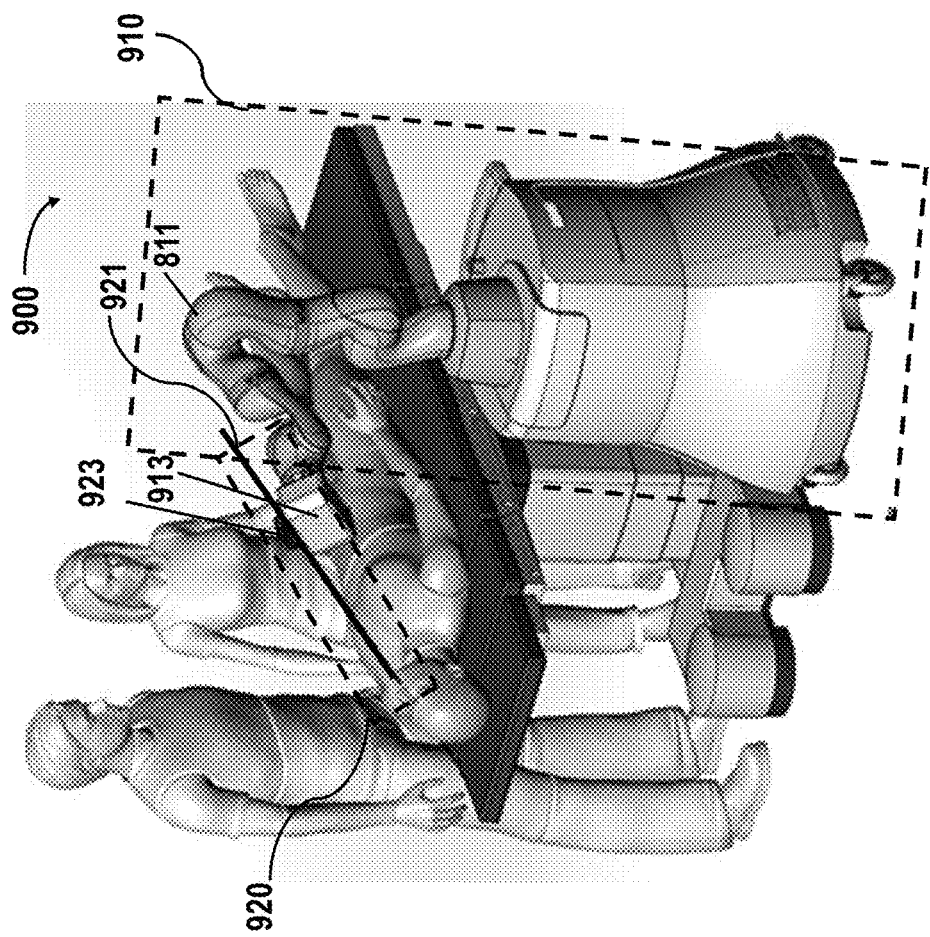

FIG. 9 show examples of robotic endoscope (e.g., bronchoscopy) system 900, 930, in accordance with some embodiments of the invention. As shown in FIG. 9, the robotic endoscope (e.g., bronchoscopy) system 900 may comprise a steerable catheter assembly 920 and a robotic support system 910, for supporting or carrying the steerable catheter assembly. The steerable catheter assembly can be a bronchoscope. The steerable catheter assembly can be the same as the endoscope device as described above. In some embodiments, the steerable catheter assembly may be a single-use robotic bronchoscope. In some embodiments, the robotic endoscope (e.g., bronchoscopy) system 900 may comprise an instrument driving mechanism (IDM) 913 that is attached to the arm of the robotic support system. The instrument driving mechanism may be provided by any suitable controller device (e.g., hand-held controller) that may or may not include a robotic system. The instrument driving mechanism may provide mechanical and electrical interface to the steerable catheter assembly 920. The mechanical interface may allow the steerable catheter assembly 920 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

The steerable catheter assembly 920 may comprise a handle portion 923 that may include components configured to processing image data, provide power, or establish communication with other external devices. For instance, the handle portion 923 may include a circuitry and communication elements that enables electrical communication between the steerable catheter assembly 920 and the instrument driving mechanism 913, and any other external system or devices. In another example, the handle portion 223 may comprise circuitry elements such as power sources for powering the electronics (e.g. camera and LED lights) of the endoscope. In some cases, the handle portion may be in electrical communication with the instrument driving mechanism 913 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 913 may provide a mechanical interface only. The handle portion may be in electrical communication with a modular wireless communication device or any other user device (e.g., portable/handheld device or controller) for transmitting sensor data and/or receiving control signals.

The steerable catheter assembly 920 may comprise a flexible elongate member 911 that is coupled to the handle portion. In some embodiments, the flexible elongate member may comprise a shaft, steerable tip and a steerable section. The steerable catheter assembly may be a single use robotic bronchoscope. In some cases, only the elongate member may be disposable. In some cases, at least a portion of the elongate member (e.g., shaft, steerable tip, etc) may be disposable. In some cases, the entire steerable catheter assembly 920 including the handle portion and the elongate member can be disposable. The flexible elongate member and the handle portion are designed such that the entire steerable catheter assembly can be disposed of at low cost.

In some embodiments, the provided bronchoscope system may also comprise a user interface. As illustrated in the example system 930, the bronchoscope system may include a treatment interface module 931 (user console side) and/or a treatment control module 933 (patient and robot side). The treatment interface module may allow an operator or user to interact with the bronchoscope during surgical procedures. In some embodiments, the treatment control module 933 may be a hand-held controller. The treatment control module 933 may allow a user to control a velocity of the tip of the bronchoscope as described elsewhere herein. The treatment control module may, in some cases, comprise a proprietary user input device and one or more add-on elements removably coupled to an existing user device to improve user input experience. For instance, physical trackball or roller can replace or supplement the function of at least one of the virtual graphical element (e.g., navigational arrow displayed on touchpad) displayed on a graphical user interface (GUI) by giving it similar functionality to the graphical element which it replaces. Examples of user devices may include, but are not limited to, mobile devices, smartphones/cellphones, tablets, personal digital assistants (PDAs), laptop or notebook computers, desktop computers, media content players, and the like. Details about the user interface device and user console are described later herein.

Figure 10:
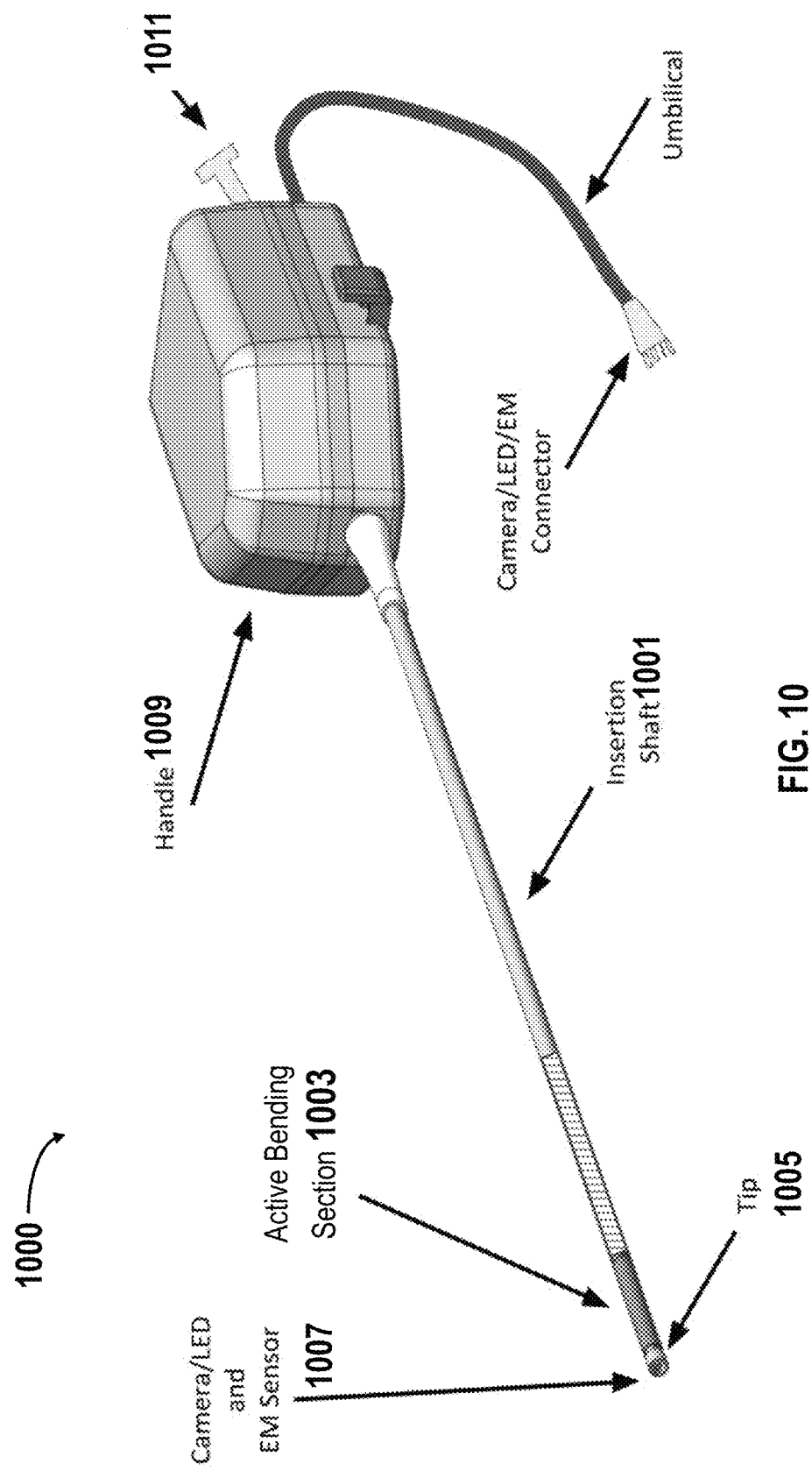
FIG. 10 illustrates an example of a flexible endoscope, in accordance with some embodiments of the present disclosure.

FIG. 10 illustrates an example of a flexible endoscope 1000, in accordance with some embodiments of the present disclosure. As shown in FIG. 10, the flexible endoscope 1000 may comprise a handle/proximal portion 1009 and a flexible elongate member to be inserted inside of a subject. The flexible elongate member can be the same as the one described above. In some embodiments, the flexible elongate member may comprise a proximal shaft (e.g., insertion shaft 1001), steerable tip (e.g., tip 1005), and a steerable section (active bending section 1003). The active bending section, and the proximal shaft section can be the same as those described elsewhere herein. The endoscope 100 may also be referred to as steerable catheter assembly as described elsewhere herein. In some cases, the endoscope 100 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of. In some embodiment, the endoscope may contain varying levels of stiffness along the shaft, as to improve functional operation.

The endoscope or steerable catheter assembly 1000 may comprise a handle portion 1009 that may include one or more components configured to process image data, provide power, or establish communication with other external devices. For instance, the handle portion may include a circuitry and communication elements that enables electrical communication between the steerable catheter assembly 1000 and an instrument driving mechanism (not shown), and any other external system or devices. In another example, the handle portion 1009 may comprise circuitry elements such as power sources for powering the electronics (e.g., camera, electromagnetic sensor and LED lights) of the endoscope.

The one or more components located at the handle may be optimized such that expensive and complicated components may be allocated to the robotic support system, a hand-held controller or an instrument driving mechanism thereby reducing the cost and simplifying the design the disposable endoscope. The handle portion or proximal portion may provide an electrical and mechanical interface to allow for electrical communication and mechanical communication with the instrument driving mechanism. The instrument driving mechanism may comprise a set of motors that are actuated to rotationally drive a set of pull wires of the catheter. The handle portion of the catheter assembly may be mounted onto the instrument drive mechanism so that its pulley/capstans assemblies are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

The electrical interface (e.g., printed circuit board) may allow image/video data and/or sensor data to be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 1009 may comprise one or more mechanical control modules such as lure 1011 for interfacing the irrigation system/aspiration system. In some cases, the handle portion may include lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 1000. The mechanical interface may allow the steerable catheter assembly 1000 to be releasably coupled to the instrument driving mechanism. For instance, the handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 1007 is located at the tip of the catheter or endoscope shaft 1005. For example, line of sight of the camera may be controlled by controlling the articulation of the active bending section 1003. In some instances, the angle of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with aid of an optimal component.

The distal tip 1005 may be a rigid component that allow for positioning sensors such as electromagnetic (EM) sensors, imaging devices (e.g., camera) and other electronic components (e.g., LED light source) being embedded at the distal tip.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient torso during procedure to locate the EM sensor position in 3D space or may locate the EM sensor position and orientation in 5D or 6D space. This may provide a visual guide to an operator when driving the bronchoscope towards the target site.

The endoscope may have a unique design in the elongate member. In some cases, the active bending section 1003, and the proximal shaft of the endoscope may consist of a single tube that incorporates a series of cuts (e.g., reliefs, slits, etc.) along its length to allow for improved flexibility, a desirable stiffness as well as the anti-prolapse feature (e.g., features to define a minimum bend radius).

As described above, the active bending section 1003 may be designed to allow for bending in two or more degrees of freedom (e.g., articulation). A greater bending degree such as 180 and 270 degrees (or other articulation parameters for clinical indications) can be achieved by the unique structure of the active bending section. In some cases, a variable minimum bend radius along the axial axis of the elongate member may be provided such that an active bending section may comprise two or more different minimum bend radii.

The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip of the endoscope, running through the bending section, and entering the handle where they are coupled to a driving component (e.g., pulley). This handle pulley may interact with an output shaft from the robotic system.

In some embodiments, the proximal end or portion of one or more pull wires may be operatively coupled to various mechanisms (e.g., gears, pulleys, capstans, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end/portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The pull wires may be made of any suitable material such as stainless steel (e.g., SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The proximal design may improve the reliability of the device without introducing extra cost allowing for a low-cost single-use endoscope. In another aspect of the invention, a single-use robotic endoscope is provided. The robotic endoscope may be a bronchoscope and can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in a pre-sterilized package and are intended to be disposed of after a single-use.

Figure 11:
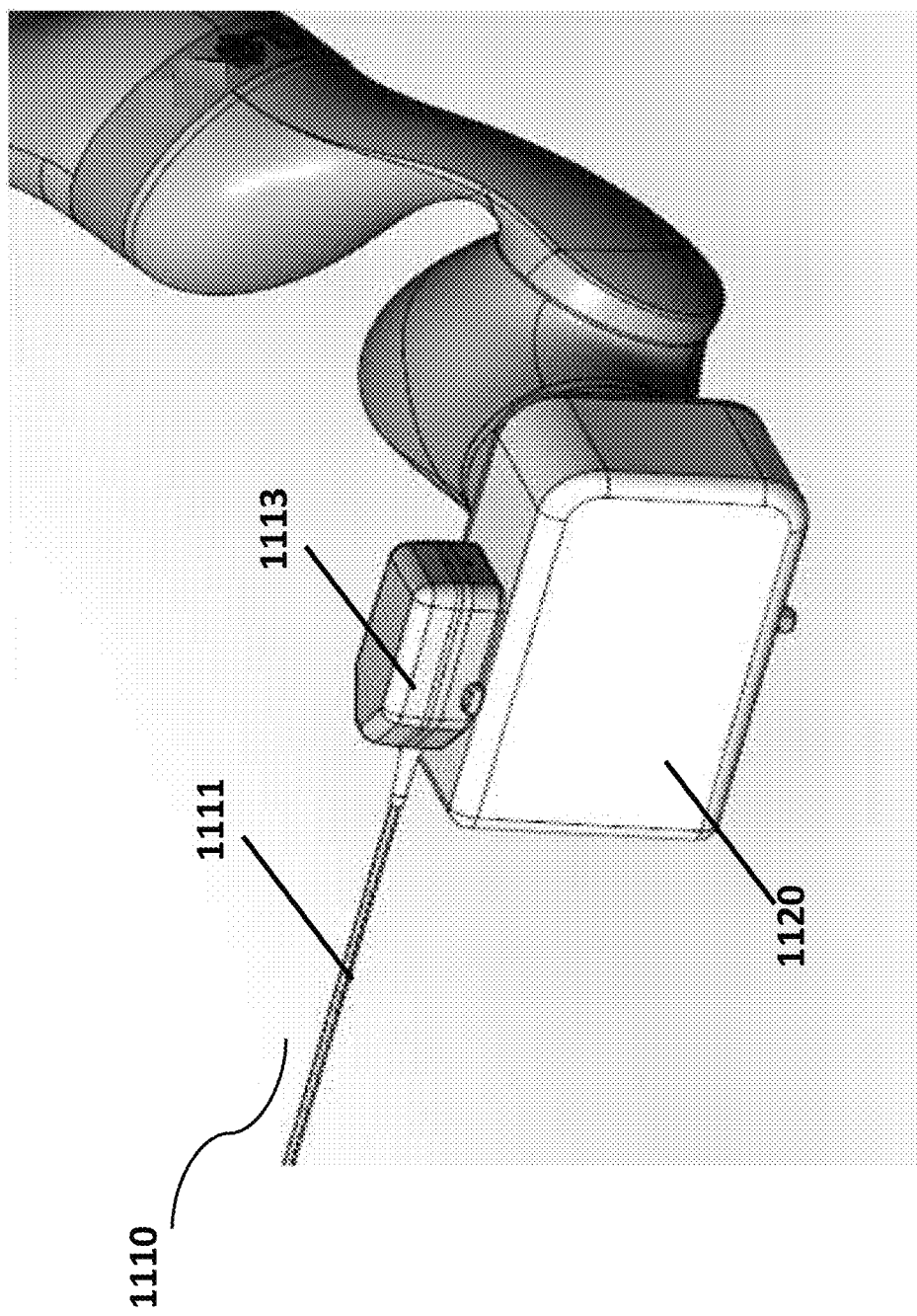
FIG. 11 shows an example of a robotic bronchoscope comprising a handle portion and a flexible elongate member.

As shown in FIG. 11, a robotic bronchoscope 1120 may comprise a handle portion 1113 and a flexible elongate member 1111. In some embodiments, the flexible elongate member 1111 may comprise a shaft, steerable tip, and a steerable/active bending section. The robotic bronchoscope 1120 can be the same as the steerable catheter assembly as described in FIG. 10. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. In some cases, the bronchoscope may contain varying levels of stiffness along its shaft, as to improve functional operation. In some cases, a minimum bend radius along the shaft may vary.

The robotic bronchoscope can be releasably coupled to an instrument driving mechanism 1120. The instrument driving mechanism 1120 may be mounted to the arm of the robotic support system or to any actuated support system as described elsewhere herein. The instrument driving mechanism may provide mechanical and electrical interface to the robotic bronchoscope 1110. The mechanical interface may allow the robotic bronchoscope 1110 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

Figure 12A:
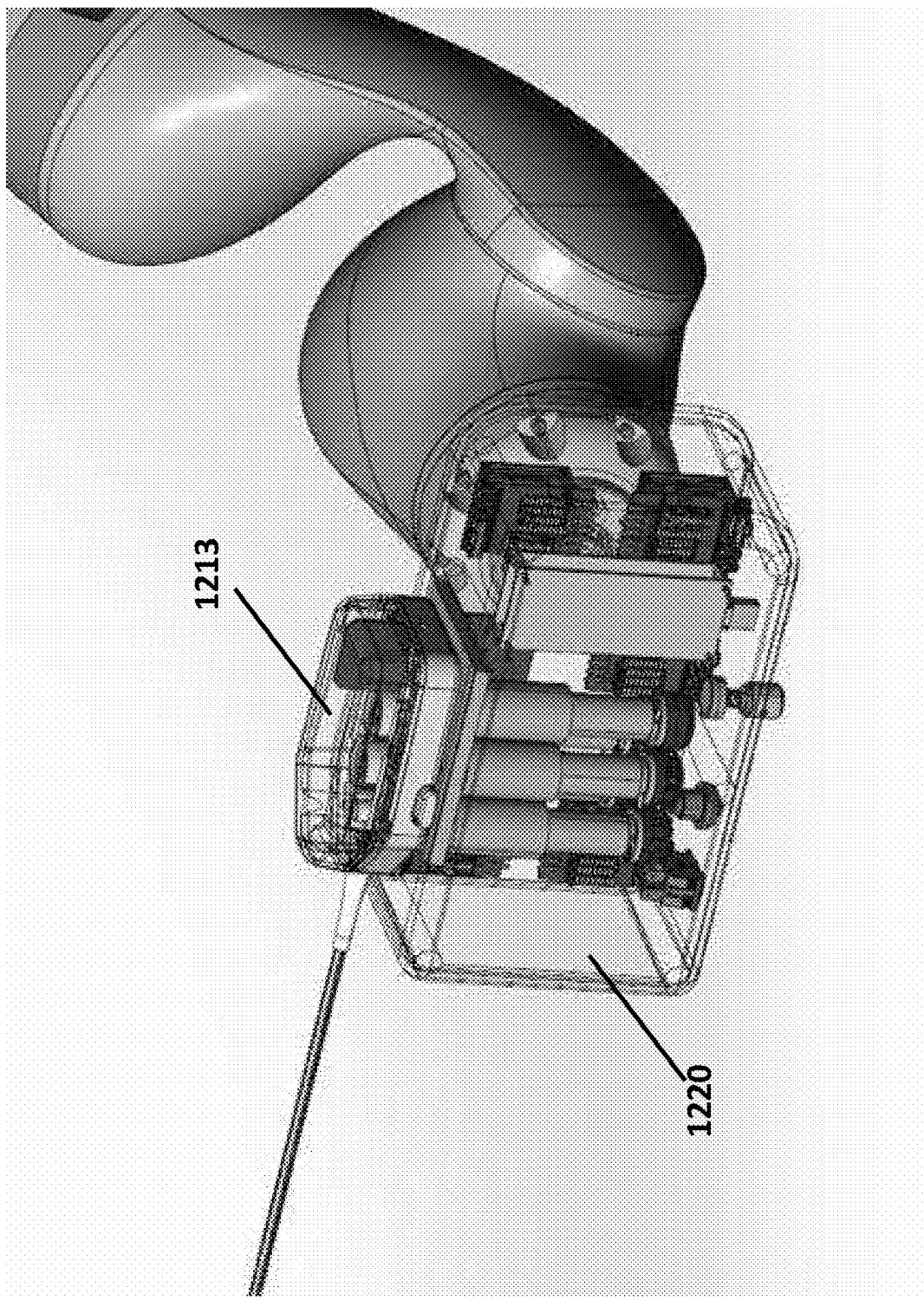
FIG. 12A shows an example of an instrument driving mechanism (IDM) providing mechanical interface to the handle portion of the robotic bronchoscope.

FIG. 12A shows an example of an instrument driving mechanism (IDM) 1220 providing mechanical interface to the handle portion 1213 of the robotic bronchoscope. As shown in the example, the instrument driving mechanism 1220 may comprise a set of motors that are actuated to rotationally drive a set of pull wires of the flexible endoscope or catheter. The handle portion 1213 of the catheter assembly may be mounted onto the instrument drive mechanism so that its pulley assemblies or capstans are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive, adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

Figure 12B:
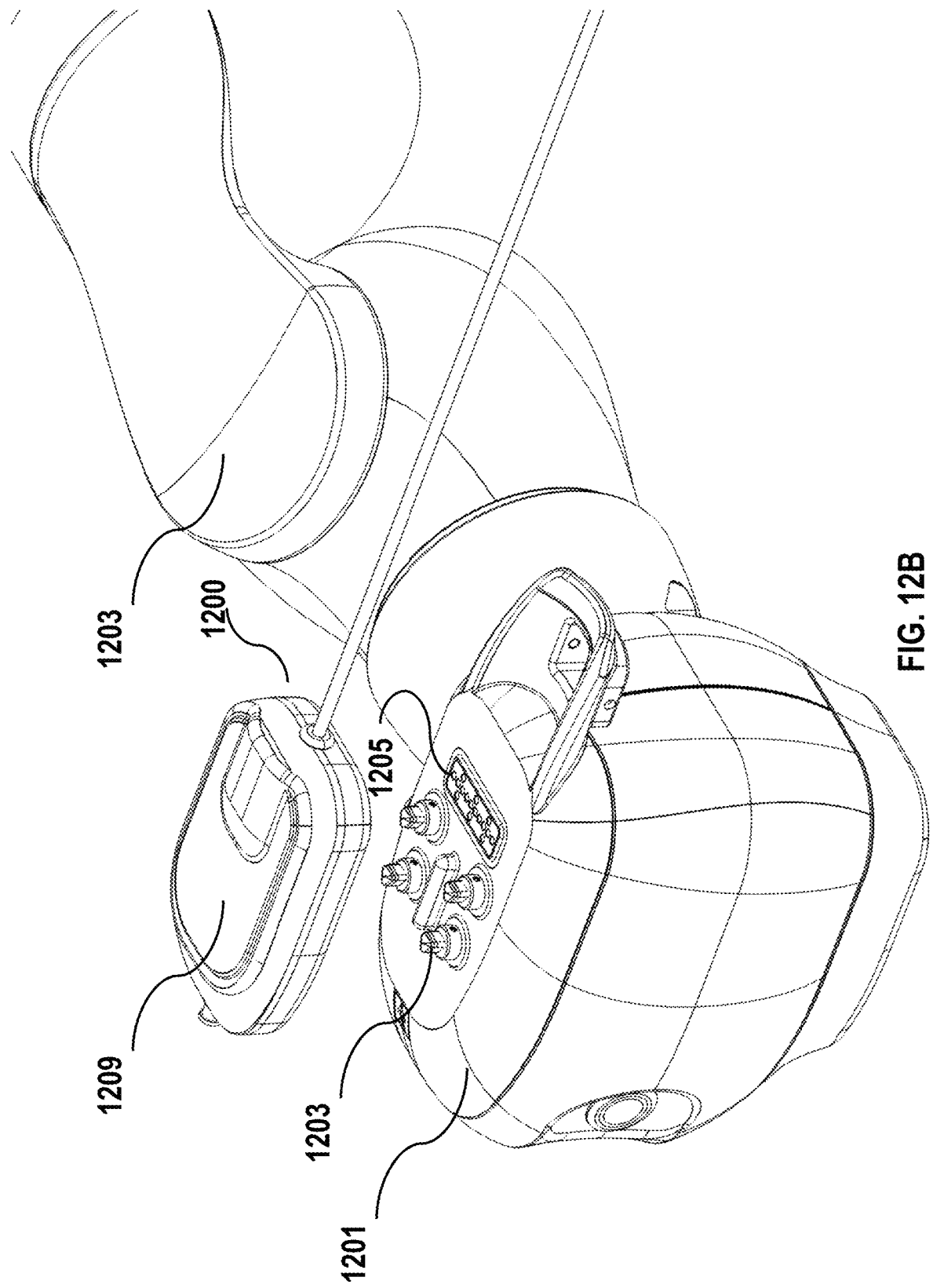
FIG. 12B shows an example of a disposable endoscope removably coupled to an IDM.

FIG. 12B shows another example of a disposable endoscope 1200 removably coupled to an IDM 1201. The one or more components located at the handle 1209 may be optimized such that expensive and complicated components may be allocated to the robotic support system 1203, a hand-held controller or an instrument driving mechanism 1201 thereby reducing the cost and simplifying the design the disposable endoscope. The handle portion or proximal portion 1209 may provide an electrical interface and mechanical interface to allow for electrical communication and mechanical communication with the instrument driving mechanism 1201. The instrument driving mechanism 1201 may comprise a set of motors that are actuated to rotationally drive a set of pull wires of the catheter. The handle portion 1209 of the catheter assembly may be mounted onto the instrument drive mechanism 1201 so that its pulley/capstans assemblies are driven by the set of motors. For example, the handle pulley may interact with an output shaft 1203 from the IDM supported by the robotic system The number of pulleys may vary based on the pull wire configurations. In some cases, one, two, three, four, or more pull wires may be utilized for articulating the flexible endoscope or catheter.

Figure 13:
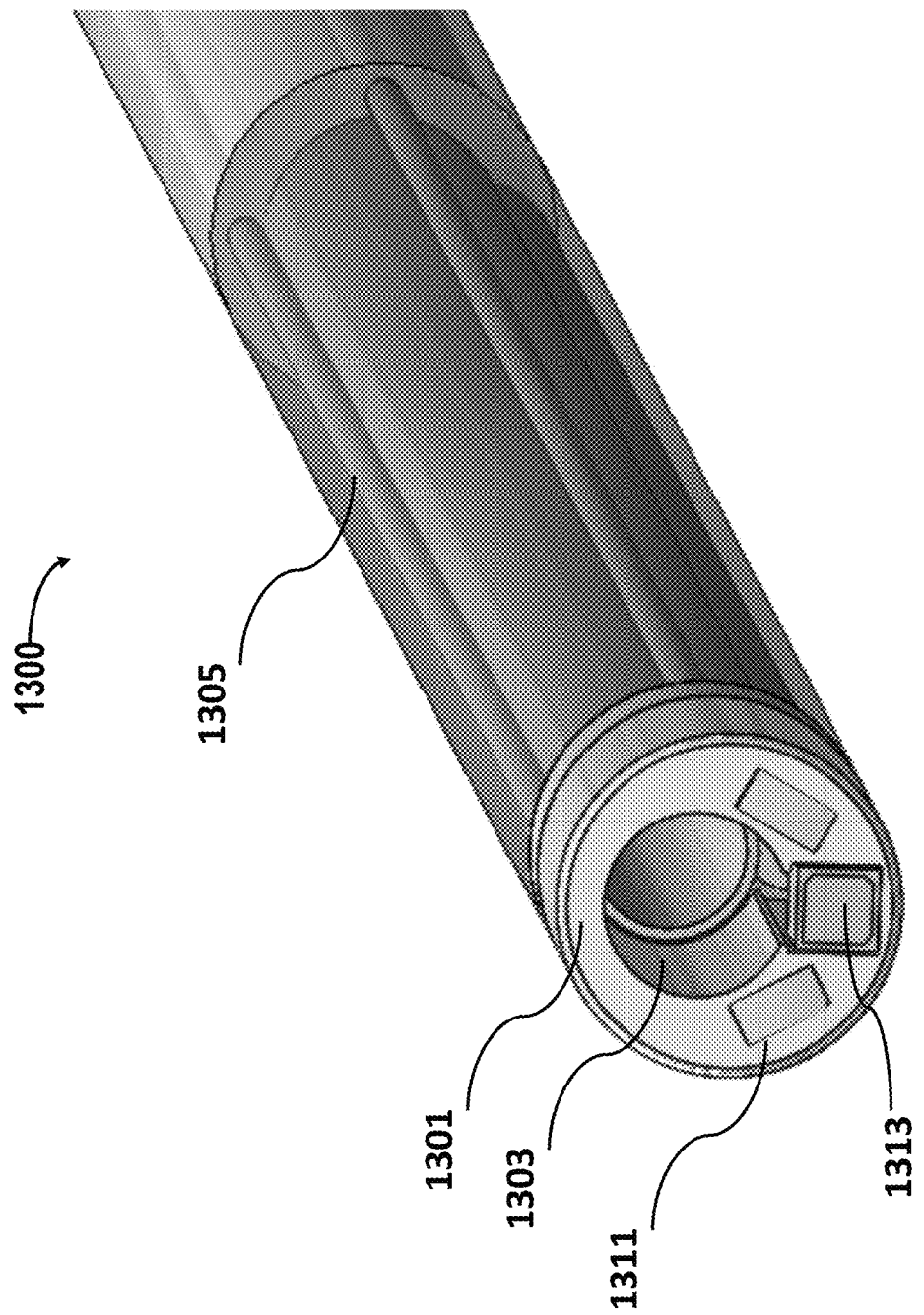
FIG. 13 shows an example of a distal tip of an endoscope.

FIG. 13 shows an example of a distal tip 1300 of an endoscope. In some cases, the distal portion or tip of the catheter 1300 may be substantially flexible such that it can be steered into one or more directions (e.g., pitch, yaw). The catheter may comprise a tip portion, bending section, and insertion shaft. In some embodiments, the catheter may have variable bending stiffness along the longitudinal axis direction. For instance, the catheter may comprise multiple sections having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some embodiments, the catheter may have variable minimum bend radius along the longitudinal axis direction. The selection of different minimum bend radius at different location long the catheter may beneficially provide anti-prolapse capability while still allow the catheter to reach hard-to-reach regions. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 1305. The distal portion of the catheter may be made of any suitable material such as co-polymers, polymers, metals or alloys such that it can be bent by the pull wires. In some embodiments, the proximal end or terminal end of one or more pull wires 1305 may be coupled to a driving mechanism (e.g., gears, pulleys, capstan etc.) via the anchoring mechanism as described above.

The pull wire 1305 may be a metallic wire, cable or thread, or it may be a polymeric wire, cable or thread. The pull wire 1305 can also be made of natural or organic materials or fibers. The pull wire 1305 can be any type of suitable wire, cable or thread capable of supporting various kinds of loads without deformation, significant deformation, or breakage. The distal end or portion of one or more pull wires 1305 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 1313. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1311 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

Figure 14:
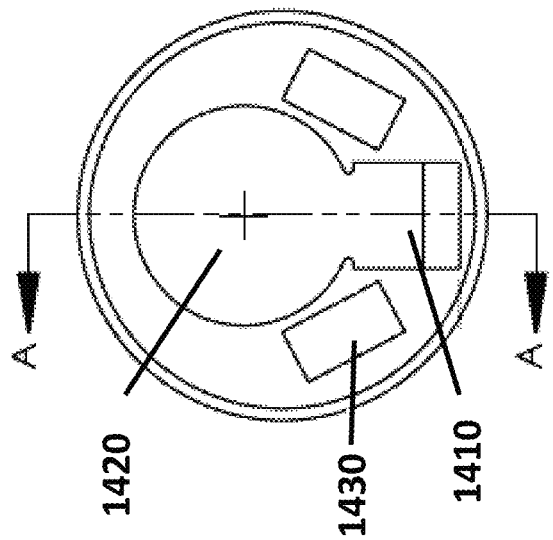
FIG. 14 shows an example distal portion of the catheter with integrated imaging device and the illumination device.
Figure 14:
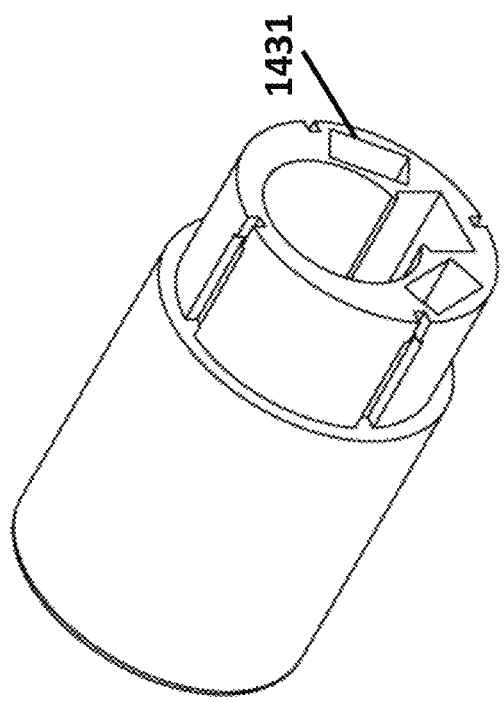

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 14 shows an example distal portion of the catheter with integrated imaging device and the illumination device. A camera may be located at the distal portion. The distal tip may have a structure to receive the camera, illumination device and/or the location sensor. For example, the camera may be embedded into a cavity 1410 at the distal tip of the catheter. The cavity 1410 may be integrally formed with the distal portion of the cavity and may have a dimension matching a length/width of the camera such that the camera may not move relative to the catheter. The camera may be adjacent to the working channel 1420 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in a wire bundle providing power to the camera as well as illumination elements or other circuitry at the distal tip of the catheter. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 1430 having a dimension matching a dimension of the miniaturized LED light source. As shown in the illustrated example, two cavities 1430 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1431 may be placed at the forwarding end face of the distal tip providing precise positioning of the LEDs as well as sufficient room for the glue. The cover 1431 may be composed of transparent material matching the refractive index of the glue so that the illumination light may not be obstructed.

Figure 15:
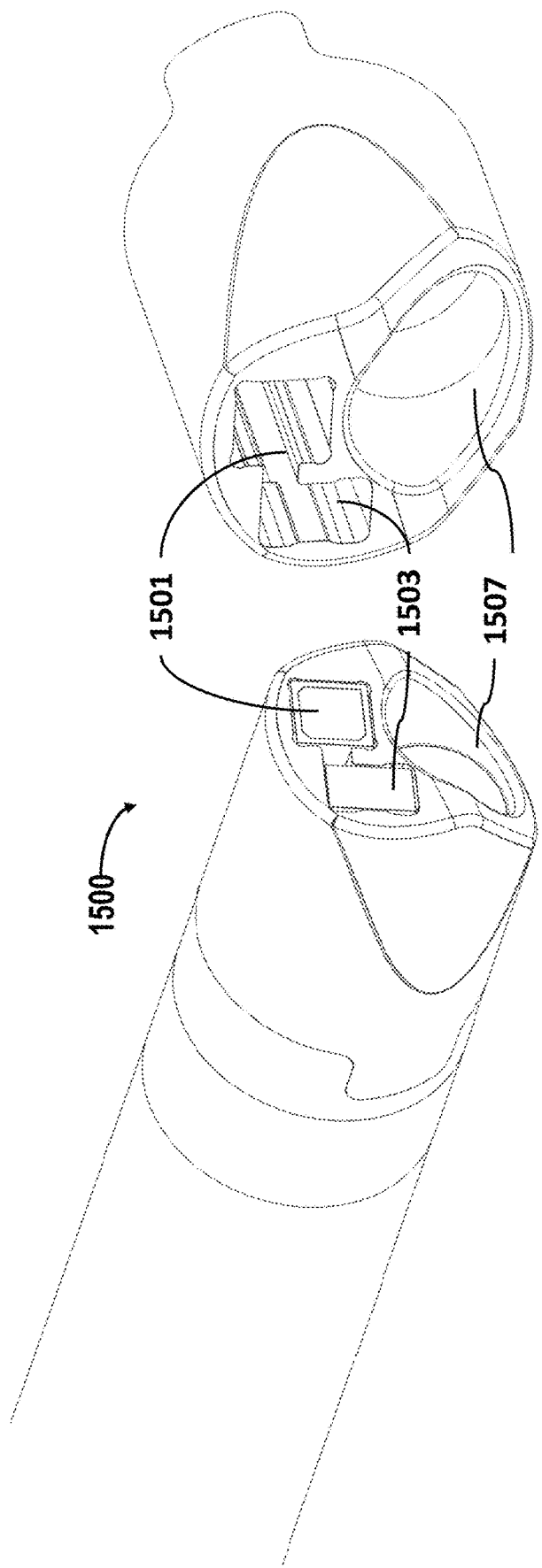
FIG. 15 shows an example of a distal portion of the catheter with integrated imaging device and the illumination device.

It should be noted that the illustrated distal end design is for illustration purpose only. There can be other suitable design for integrating the one or more components into the distal tip. FIG. 15 shows another example of a distal portion 1500 of the catheter with integrated imaging device and the illumination device. As shown in the example 1500, the distal tip may have a structure 1501 to receive the camera, a structure 1503 to receive an illumination device and/or the location sensor. The camera may be embedded into a cavity 1501 at the distal tip of the catheter. The cavity 1501 may be integrally formed with the distal portion of the cavity and may have a dimension matching a length/width of the camera such that the camera may not move relative to the catheter. The camera may be adjacent to the working channel 1507 of the catheter to provide near field view of the tissue or the organs. In some cases, the attitude or orientation of the imaging device may be controlled by controlling a rotational movement (e.g., roll) of the catheter. As shown in the illustrated example 1500, a cavity 1503 may be integrally formed with the catheter to receive an LED light source.

In an aspect, a system for controlling a tip motion of an articulating flexible endoscope is provided. The system comprises: a memory storing computer-executable instructions; one or more processors in communication with the articulating flexible endoscope and configured to execute the computer-executable instructions to: generate a command to drive an elongated member of the articulating flexible endoscope along an anatomical pathway via an instrument driving mechanism (IDM); receive sensor data acquired by a position sensor disposed at a distal tip portion of the elongated member; upon determining the distal tip portion is at a pre-selected location within the anatomical pathway, set a motion of the distal tip to zero and calculate the motion of the distal tip portion within a time window; calculate a disparity between the motion of the distal tip portion and a motion of the IDM within the same time window; and detect a buckling event by comparing the disparity to a threshold.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU) or a microcontroller), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

The one or more processors may be in communication with the endoscope. The one or more processor may be located remotely from the endoscope system or onboard of the endoscope system (e.g., located at the handle, located at the user device for controlling the endoscope).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for controlling a tip motion of an articulating flexible endoscope, the method comprising:
generating a command to drive an elongated member of the articulating flexible endoscope along an anatomical pathway via an instrument driving mechanism (IDM);
receiving sensor data acquired by a position sensor disposed at a distal tip portion of the elongated member;
upon determining the distal tip portion is at a pre-selected location within the anatomical pathway, setting a motion of the distal tip to zero and calculating the motion of the distal tip portion within a time window;
calculating a disparity between the motion of the distal tip portion projected in a heading direction and a motion of the IDM along an insertion direction within the same time window;
determining a dynamic threshold along the insertion direction, wherein the dynamic threshold is varied based at least in part on an insertion distance; and
detecting a buckling event by comparing the disparity to the dynamic threshold.

2. The method of claim 1, wherein the pre-selected location comprises a main carina location.

3. The method of claim 1, further comprising determining the distal tip portion is at the pre-selected location based at least in part on the sensor data and a 3D model of the anatomical pathway.

4. The method of claim 1, further comprising determining the distal tip portion is at the preselected location based at least in part on image data acquired by a camera located at the distal tip portion.

5. The method of claim 1, wherein a size of the time window is between four seconds to eight seconds.

6. The method of claim 5, wherein the size of the time window is determined based on empirical data.

7. The method of claim 1, wherein the motion of the distal tip portion within the time window is an accumulation of distance traveled at each time step.

8. The method of claim 1, further comprising setting an insertion force applied by the IDM to zero upon determining the distal tip portion is at the pre-selected location within the anatomical pathway and comparing the insertion force with a force threshold.

9. The method of claim 8, further comprising generating and displaying a warning message on a user interface upon determining the insertion force is above the force threshold.

10. The method of claim 1, wherein the disparity in motion comprises a disparity between an expected velocity and a tip velocity of the distal tip portion measured based on the sensor data.

11. The method of claim 10, wherein the tip velocity is calculated as a filtered time derivative of the sensor data projected in the heading direction.

12. The method of claim 11, wherein the tip velocity is processed by a low-pass filter to be utilized as a feedback signal for a closed loop control.

13. The method of claim 11, wherein the sensor data is acquired within a frequency range of 10-60 Hz.

14. The method of claim 10, wherein the expected velocity is based on an input command.

15. The method of claim 1, wherein the distal tip portion comprises a structure to receive an imaging device, the position sensor, and an illumination device.

16. The method of claim 1, wherein a proximal end of the elongated member of the articulating flexible endoscope is connected to IDM for applying a force to one or more pull wires for articulating the distal tip portion of the elongated member, inserting or retracting the articulating flexible endoscope.

17. The method of claim 1, further comprising displaying, on a user interface, a message indicative of the buckling event and a recommendation for taking an action in response to the buckling event.

18. The method of claim 17, wherein the action in response to the buckling event comprises taking a fluoroscopic image of at least a portion of the articulating flexible endoscope.

19. A system for controlling a tip motion of an articulating flexible endoscope, the system comprising: a memory storing computer-executable instructions; one or more processors in communication with the articulating flexible endoscope and configured to execute the computer-executable instructions to:
generate a command to drive an elongated member of the articulating flexible endoscope along an anatomical pathway via an instrument driving mechanism (IDM);
receive sensor data acquired by a position sensor disposed at a distal tip portion of the elongated member;
upon determining the distal tip portion is at a pre-selected location within the anatomical pathway, set a motion of the distal tip to zero and calculate the motion of the distal tip portion within a time window;
calculate a disparity between the motion of the distal tip portion projected in a heading direction and a motion of the IDM along an insertion direction within the same time window;
determine a dynamic threshold along the insertion direction, wherein the dynamic threshold is varied based at least in part on an insertion distance; and
detect a buckling event by comparing the disparity to the dynamic threshold.

* * * * *